US008497271B2

(12) United States Patent
Bi et al.

(10) Patent No.: US 8,497,271 B2
(45) Date of Patent: Jul. 30, 2013

(54) MODULATORS OF G PROTEIN-COUPLED RECEPTOR 88

(75) Inventors: Yingzhi Bi, Plainsboro, NJ (US); Carolyn Diane Dzierba, Middletown, CT (US); Joanne J. Bronson, Durham, CT (US); Kenneth Carson, Princeton, NJ (US); Giovanni Cianchetta, Lawrenceville, NJ (US); Li Dong, Roselle Park, NJ (US); Cynthia Fink, Lebanon, NJ (US); Michael Green, Easton, PA (US); David Kimball, East Windsor, NJ (US); John E. Macor, Guilford, CT (US); Soojin Kwon, Haworth, NJ (US); Jiancheng Wang, Revere, MA (US); Yulian Zhang, Yardley, PA (US); Greg Zipp, Robbinsville, NJ (US)

(73) Assignees: Bristol-Myers Squibb Company, Princeton, NJ (US); Lexicon Pharmaceuticals, Inc., The Woodlands, TX (US)

( * ) Notice: Subject to any disclaimer, the term of this patent is extended or adjusted under 35 U.S.C. 154(b) by 278 days.

(21) Appl. No.: 12/895,916

(22) Filed: Oct. 1, 2010

(65) Prior Publication Data

US 2011/0245264 A1  Oct. 6, 2011

Related U.S. Application Data

(60) Provisional application No. 61/249,465, filed on Oct. 7, 2009.

(51) Int. Cl.
*A61K 31/496* (2006.01)
*A61K 31/165* (2006.01)
*A61K 31/381* (2006.01)
*A61P 25/16* (2006.01)
*A61P 25/18* (2006.01)
*A61P 25/28* (2006.01)
*A61P 25/30* (2006.01)
*C07C 233/60* (2006.01)
*C07D 333/24* (2006.01)
*C07D 409/12* (2006.01)

(52) U.S. Cl.
USPC ...... 514/252.13; 514/123; 514/438; 544/379; 549/77; 564/182

(58) Field of Classification Search
USPC ........ 514/252.13, 123, 438; 544/379; 549/77; 564/182
See application file for complete search history.

(56) References Cited

U.S. PATENT DOCUMENTS

| 6,172,091 B1 * | 1/2001 | Cohen et al. | 514/357 |
| 7,834,013 B2 * | 11/2010 | Corbett et al. | 514/237.8 |
| 7,915,448 B2 * | 3/2011 | Hanazawa et al. | 564/99 |

FOREIGN PATENT DOCUMENTS

| CN | 1733708 | 2/2006 |
| JP | 2007-217408 | 8/2007 |
| WO | WO 94/12461 | 6/1994 |
| WO | WO 96/21464 | 7/1996 |
| WO | WO 0021910 | * 4/2000 |
| WO | WO 03/086325 | 10/2003 |
| WO | WO03/103666 A2 | 12/2003 |
| WO | WO2004/047738 A2 | 6/2004 |
| WO | WO 2004/056745 | 7/2004 |
| WO | WO 2004/072018 | 8/2004 |
| WO | WO 2005/000309 | 1/2005 |
| WO | WO2005/051890 A1 | 6/2005 |
| WO | WO 2006/012227 | 2/2006 |
| WO | WO2006/027252 A1 | 3/2006 |
| WO | WO 2006097817 | * 9/2006 |
| WO | WO 2007/117715 | 10/2007 |
| WO | WO2007/129188 A1 | 11/2007 |
| WO | WO 2008/022154 | 2/2008 |
| WO | WO 2011/044212 | 4/2011 |
| WO | WO 2011/044225 | 4/2011 |

OTHER PUBLICATIONS

Garrido, Dulce M., et al, "Synthesis and Activity of Small Molecule GPR40 Agonists," Bioorganic & Medicinal Chemistry Letters, vol. 16, No. 7, pp. 1840-1845, 2006.
U.S. Appl. No. 12/897,004, filed Oct. 4, 2010, Bi et al.
U.S. Appl. No. 12/898,016, filed Oct. 5, 2010, Dzierba et al.

* cited by examiner

*Primary Examiner* — Sreeni Padmanabhan
*Assistant Examiner* — Uma Ramachandran
(74) *Attorney, Agent, or Firm* — Pamela A. Mingo; Gary D. Greenblatt

(57) ABSTRACT

The present disclosure is generally directed to compounds which can modulate G-protein coupled receptor 88, compositions comprising such compounds, and methods for modulating G-protein coupled receptor 88.

15 Claims, No Drawings

MODULATORS OF G PROTEIN-COUPLED RECEPTOR 88

CROSS-REFERENCE TO RELATED APPLICATIONS

This application claims the benefit of U.S. provisional application Ser. No. 61/249,465 filed Oct. 7, 2009.

The present disclosure is generally directed to compounds which can modulate G-protein coupled receptor 88, compositions comprising such compounds, and methods for modulating G-protein coupled receptor 88.

GPR88 is an orphan member of the G protein coupled receptor (GPCR) superfamily. GPR88 demonstrates GPCR activity several assays including GTPgS binding, calcium influx, and cAMP inhibition assays. The receptor exhibits high expression in the CNS, with measurable expression in peripheral tissues including liver. CNS expression is particularly robust in striatum, paralleling that of the dopamine D2 receptor (Mizushima et. al, *Genomics* 69, 314-321 (2000)) suggesting the receptor may play a role in regulating dopaminergic activity. Consistent with this, genetically-modified mice that lack GPR88 expression exhibit enhanced response to dopaminergic agonists, altered performance in models relevant to schizophrenia (prepulse inhibition, conditioned avoidance responding) and depression (forced swim test). These results demonstrate therapeutic potential for GPR88 in treating CNS diseases. Transcriptional profiling studies have also revealed GPR88 expression is altered by treatments or conditions related to bipolar disorder (Ogden et al., *Mol Psychiatry* 2004 November; 9(11):1007-29 and Brandish, et al. Neuron, Vol. 45, 861-872, Mar. 24, 2005, schizophrenia (Matsuoka, et al. *Synapse* 2008 January; 62(1):1-7), and depression (Conti et al., Mol Psychiatry. 2007 February; 12(2):167-89.), providing additional support for GPR88 as an essential modulator of CNS signaling pathways related to psychiatric disease.

GPR88 is also expressed liver tissue suggesting GPR88 signaling may contribute to regulation of metabolic processes. Initial phenotypic characterization of genetically-modified mice lacking GPR88 expression (Level 1 data) suggests these animals exhibit altered response to glucose, insulin levels and triglycerides. These results suggest compounds that modulate GPR88 activity may have utility in metabolic diseases.

Based on these data, compounds that modulate GPR88 activity (agonists, antagonists, or modulators) are predicted to have therapeutic utility in the treatment of psychosis, cognitive deficits in schizophrenia, affective disorders, attention deficit hyperactivity disorders, bipolar disorder, drug addiction, Parkinson's disease, Alzheimer's disease, obesity and diabetes.

In a first aspect the present disclosure provides a compound of Formula (I)

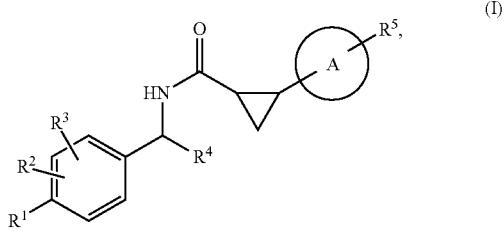

(I)

or a pharmaceutically acceptable salt thereof, wherein

A is selected from phenyl and thienyl;

$R^1$ is selected from $C_2$-$C_6$ alkenyl; $C_3$-$C_6$ alkoxy; $C_3$-$C_6$ alkylsulfanyl; $C_2$-$C_6$ alkynyl; $C_3$-$C_6$ cycloalkyl-$C_2$-$C_4$ alkenyl; $C_3$-$C_6$ cycloalkyl-$C_1$-$C_3$ alkoxy; $C_3$-$C_6$ cycloalkyloxy; phenoxy optionally substituted with one $C_1$-$C_3$ alkyl group; phenyl optionally substituted with one, two, or three groups independently selected from $C_1$-$C_3$ alkoxy, $C_1$-$C_3$ alkoxy-$C_1$-$C_3$ alkyl, $C_1$-$C_3$ alkyl, $C_1$-$C_3$ alkylsulfonyl, cyano, halo, and halo-$C_1$-$C_3$ alkyl; phenyl-$C_1$-$C_3$ alkoxy wherein the phenyl part is optionally substituted with one or two groups independently selected from $C_1$-$C_3$ alkyl and halo; and thienyl;

$R^2$ is selected from hydrogen; $C_1$-$C_3$ alkoxy; $C_1$-$C_3$ alkyl; and halo;

$R^3$ is selected from hydrogen and $C_1$-$C_3$ alkoxy;

$R^4$ is selected from $C_1$-$C_3$ alkoxy-$C_1$-$C_3$ alkyl; $C_1$-$C_6$ alkyl; heterocyclyl; hydroxy-$C_1$-$C_3$ alkyl; ($R^a R^b N$)—$C_1$-$C_3$ alkyl;

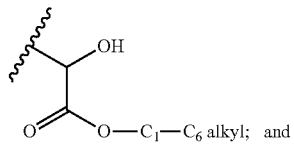

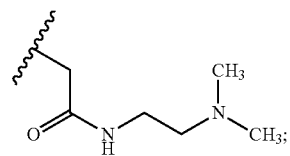

wherein 〰 denotes the point of attachment to the parent molecular moiety;

$R^5$ is selected from hydrogen and halo; and $R^a$ and $R^b$ are independently selected from hydrogen and $C_1$-$C_3$ alkyl; or $R^a$ and $R^b$, together with the nitrogen atom to which they are attached, form a piperidinyl or piperazinyl ring wherein each ring is optionally substituted with one group selected from $C_1$-$C_3$ alkyl and hydroxy-$C_1$-$C_3$ alkyl.

In a first embodiment of the first aspect $R^3$ is hydrogen. In a second embodiment A is phenyl. In a third embodiment $R^4$ is selected from $C_1$-$C_3$ alkoxy-$C_1$-$C_3$ alkyl; hydroxy-$C_1$-$C_3$ alkyl; and

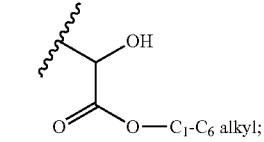

wherein 〰 denotes the point of attachment to the parent molecular moiety.

In a fourth embodiment of the first aspect the present disclosure provides a compound of formula (I), or a pharmaceutically acceptable salt thereof, wherein $R^3$ is hydrogen, A is phenyl, and $R^4$ is selected from $C_1$-$C_6$ alkyl and

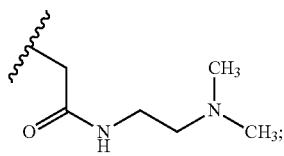 [SMILES: *CC(=O)NCCN(C)C]

wherein ⌇ denotes the point of attachment to the parent molecular moiety.

In a fifth embodiment of the first aspect the present disclosure provides a compound of formula (I), or a pharmaceutically acceptable salt thereof, wherein $R^3$ is hydrogen, A is phenyl, and $R^4$ is heterocyclyl.

In a sixth embodiment of the first aspect the present disclosure provides a compound of formula (I), or a pharmaceutically acceptable salt thereof, wherein $R^3$ is hydrogen, A is phenyl, and $R^4$ is $(R^a R^b N)$—$C_1$-$C_3$ alkyl.

In a seventh embodiment of the first aspect the present disclosure provides a compound of formula (I), or a pharmaceutically acceptable salt thereof, wherein $R^3$ is hydrogen and A is thienyl. In an eighth embodiment $R^4$ is selected from $C_1$-$C_3$ alkoxy-$C_1$-$C_3$ alkyl; hydroxy-$C_1$-$C_3$ alkyl; and

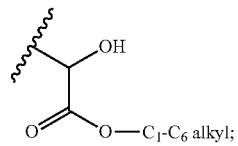

wherein ⌇ denotes the point of attachment to the parent molecular moiety.

In a ninth embodiment of the first aspect the present disclosure provides a compound of formula (I), or a pharmaceutically acceptable salt thereof, wherein $R^3$ is hydrogen and A is thienyl, and $R^4$ is selected from $C_1$-$C_6$ alkyl and

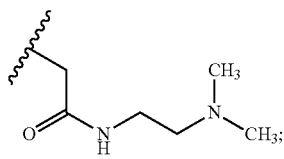 [SMILES: *CC(=O)NCCN(C)C]

wherein ⌇ denotes the point of attachment to the parent molecular moiety.

In a tenth embodiment of the first aspect the present disclosure provides a compound of formula (I), or a pharmaceutically acceptable salt thereof, wherein $R^3$ is hydrogen and A is thienyl, and $R^4$ is heterocyclyl.

In an eleventh embodiment of the first aspect the present disclosure provides a compound of formula (I), or a pharmaceutically acceptable salt thereof, wherein $R^3$ is hydrogen and A is thienyl, and $R^4$ is $(R^a R^b N)$—$C_1$-$C_3$ alkyl.

In a second aspect the present disclosure provides a compound of Formula (II)

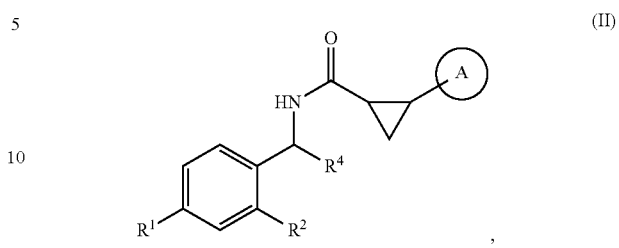

or a pharmaceutically acceptable salt thereof, wherein
A is selected from phenyl and thienyl;
$R^1$ is selected from $C_5$-$C_6$ alkoxy; $C_5$ alkynyl; phenyl optionally substituted with one group selected from $C_1$ alkoxy and $C_1$-$C_2$ alkyl;
$R^2$ is selected from hydrogen; $C_1$ alkoxy and $C_1$ alkyl;
$R^4$ is selected from hydroxy-$C_1$ alkyl and $(R^a R^b N)$—$C_1$ alkyl; and
$R^a$ and $R^b$ are independently selected from hydrogen; or
$R^a$ and $R^b$, together with the nitrogen atom to which they are attached, form a piperazinyl ring substituted with one $C_1$ alkyl group.

In a third aspect the present disclosure provides a composition comprising a compound of Formula (I), or a pharmaceutically acceptable salt thereof, and a pharmaceutically acceptable carrier.

In a fourth aspect the present disclosure provides a method of treating a disorder selected from a neurological disorder or a metabolic disease in a mammal, comprising administering to the mammal a therapeutically effective amount of a compound of Formula (I), or a pharmaceutically acceptable salt thereof. In a first embodiment of the fourth aspect the mammal is a human. In a second embodiment of the fourth aspect the disorder is a neurological disorder is selected from psychosis, cognitive deficits in schizophrenia, affective disorders, attention deficit hyperactivity disorders, drug addiction, Parkinson's disease, and Alzheimer's disease. In a third embodiment of the fourth aspect the disorder is a metabolic disease selected from obesity and diabetes.

In a fifth aspect the present disclosure provides a method of modulating G protein-coupled receptor 88 in a mammal, comprising administering to the mammal a therapeutically effective amount of a compound of Formula (I), or a pharmaceutically acceptable salt thereof. In a first embodiment of the fifth aspect the mammal is a human. In a second embodiment of the fifth aspect the G protein-coupled receptor 88 is modulated in order to treat a neurological disorder or metabolic disease. In a third embodiment of the fifth aspect the G protein-coupled receptor 88 is modulated in order to treat a neurological disorder wherein the neurological disorder is selected from psychosis, cognitive deficits in schizophrenia, affective disorders, attention deficit hyperactivity disorders, bipolar disorder, drug addiction, Parkinson's disease, and Alzheimer's disease. In a fourth embodiment of the fifth aspect the G protein-coupled receptor 88 is modulated in order to treat a metabolic disease wherein the metabolic disease is selected from obesity and diabetes.

Other embodiments of the present disclosure may comprise suitable combinations of two or more of embodiments and/or aspects disclosed herein.

Yet other embodiments and aspects of the disclosure will be apparent according to the description provided below.

The description of the present disclosure herein should be construed in congruity with the laws and principals of chemical bonding. In some instances it may be necessary to remove a hydrogen atom in order accommodate a substitutent at any given location.

It should be understood that the compounds encompassed by the present disclosure are those that are suitably stable for use as pharmaceutical agent.

All patents, patent applications, and literature references cited in the specification are herein incorporated by reference in their entirety. In the case of inconsistencies, the present disclosure, including definitions, will prevail.

As used in the present specification, the following terms have the meanings indicated:

As used herein, the singular forms "a", "an", and "the" include plural reference unless the context clearly dictates otherwise.

In some instances, the number of carbon atoms in any particular group is denoted before the recitation of the group. For example, the term "$C_{2-6}$ alkenyl" denotes an alkenyl group containing two to six carbon atoms. Where these designations exist they supercede all other definitions contained herein.

The term "alkenyl," as used herein, refers to a straight or branched chain group of two to six carbon atoms containing at least one carbon-carbon double bond.

The term "alkoxy," as used herein, refers to an alkyl group attached to the parent molecular moiety through an oxygen atom.

The term "alkoxyalkyl," as used herein, refers to an alkyl group substituted with one, two, or three alkoxy groups.

The term "alkyl," as used herein, refers to a group derived from a straight or branched chain saturated hydrocarbon containing from one to six carbon atoms.

The term "alkylsulfanyl," as used herein, refers to an alkyl group attached to the parent molecular moiety through a sulfur atom.

The term "alkylsulfonyl," as used herein, refers to an alkyl group attached to the parent molecular moiety through a sulfonyl group.

The term "alkynyl," as used herein, refers to a straight or branched chain group of two to six carbon atoms containing at least one carbon-carbon triple bond.

The term "cyano," as used herein, refers to —CN.

The term "cycloalkyl," as used herein, refers to a saturated monocyclic, hydrocarbon ring system having three to seven carbon atoms and zero heteroatoms. Representative examples of cycloalkyl groups include, but are not limited to, cyclopropyl, cyclopentyl, and cyclohexyl.

The term "(cycloalkyl)alkenyl," as used herein, refers to an alkenyl group substituted with one, two, or three cycloalkyl groups.

The term "(cycloalkyl)alkoxy," as used herein, refers to a cycloalkyl group attached to the parent molecular moiety through an alkoxy group.

The term "cycloalkyloxy," as used herein, refers to a cycloalkyl group attached to the parent molecular moiety through an oxygen atom.

The terms "halo" and "halogen," as used herein, refer to F, Cl, Br, or I.

The term "haloalkyl," as used herein, refers to an alkyl group substituted by one, two, three, or four halogen atoms.

The term "heterocyclyl," as used herein, refers to a four-, five-, six-, or seven-membered ring containing one, two, three, or four heteroatoms independently selected from nitrogen, oxygen, and sulfur. The four-membered ring has zero double bonds, the five-membered ring has zero to two double bonds, and the six- and seven-membered rings have zero to three double bonds. The term "heterocyclyl" also includes bicyclic groups in which the heterocyclyl ring is fused to another monocyclic heterocyclyl group, or a four- to six-membered aromatic or non-aromatic carbocyclic ring; as well as bridged bicyclic groups such as 7-azabicyclo[2.2.1]hept-7-yl, 2-azabicyclo[2.2.2]oc-2-tyl, and 2-azabicyclo[2.2.2]oc-3-tyl. The heterocyclyl groups of the present disclosure can be attached to the parent molecular moiety through any carbon atom or nitrogen atom in the group. Examples of heterocyclyl groups include, but are not limited to, benzothienyl, furyl, imidazolyl, indolinyl, indolyl, isothiazolyl, isoxazolyl, morpholinyl, oxazolyl, piperazinyl, piperidinyl, pyrazolyl, pyridinyl, pyrrolidinyl, pyrrolopyridinyl, pyrrolyl, thiazolyl, thienyl, thiomorpholinyl, 7-azabicyclo[2.2.1]hept-7-yl, 2-azabicyclo[2.2.2]oc-2-tyl, and 2-azabicyclo[2.2.2]oc-3-tyl.

The term "hydroxy," as used herein, refers to —OH.

The term "hydroxyalkyl," as used herein, refers to an alkyl group substituted with one, two, or three hydroxy groups.

The term "—$NR^aR^b$," as used herein, refers to two groups, $R^a$ and $R^b$, which are attached to the parent molecular moiety through a nitrogen atom. $R^a$ and $R^b$ are independently selected from hydrogen and $C_1$-$C_3$ alkyl, or, alternatively, $R^a$ and $R^b$, together with the nitrogen atom to which they are attached, form a piperidinyl or piperazinyl ring wherein each ring is optionally substituted with one group selected from $C_1$-$C_3$ alkyl and hydroxy-$C_1$-$C_3$ alkyl.

The term "($NR^aR^b$)alkyl," as used herein, refers to an alkyl group substituted with one, two, or three —$NR^aR^b$ groups.

The term "phenoxy," as used herein, refers to a phenyl group attached to the parent molecular moiety through an oxygen atom.

The term "phenylalkoxy," as used herein, refers to a phenyl group attached to the parent molecular moiety through an alkoxy group.

The term "sulfonyl," as used herein, refers to —$SO_2$—.

Asymmetric centers exist in the compounds of the present disclosure. These centers are designated by the symbols "R" or "S", depending on the configuration of substituents around the chiral carbon atom. It should be understood that the disclosure encompasses all stereochemical isomeric forms, or mixtures thereof, which possess the ability to modulate G protein-coupled receptor 88. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, or direct separation of enantiomers on chiral chromatographic columns. Starting compounds of particular stereochemistry are either commercially available or can be made and resolved by techniques known in the art.

Certain compounds of the present disclosure may also exist in different stable conformational forms which may be separable. Torsional asymmetry due to restricted rotation about an asymmetric single bond, for example because of steric hindrance or ring strain, may permit separation of different conformers. The present disclosure includes each conformational isomer of these compounds and mixtures thereof.

The term "compounds of the present disclosure", and equivalent expressions, are meant to embrace compounds of Formula (I), and pharmaceutically acceptable enantiomers, diastereomers, and salts thereof. Similarly, references to intermediates are meant to embrace their salts where the context so permits.

The compounds of the present disclosure can exist as pharmaceutically acceptable salts. The term "pharmaceutically acceptable salt," as used herein, represents salts or zwitterionic forms of the compounds of the present disclosure which are water or oil-soluble or dispersible, which are, within the scope of sound medical judgment, suitable for use in contact with the tissues of patients without excessive toxicity, irritation, allergic response, or other problem or complication commensurate with a reasonable benefit/risk ratio, and are effective for their intended use. The salts can be prepared during the final isolation and purification of the compounds or separately by reacting a suitable nitrogen atom with a suitable acid. Representative acid addition salts include acetate, adipate, alginate, citrate, aspartate, benzoate, benzenesulfonate, bisulfate, butyrate, camphorate, camphorsulfonate; digluconate, dihydrobromide, dihydrochloride, dihydroiodide, glycerophosphate, hemisulfate, heptanoate, hexanoate, formate, fumarate, hydrochloride, hydrobromide, hydroiodide, 2-hydroxyethanesulfonate, lactate, maleate, mesitylenesulfonate, methanesulfonate, naphthylenesulfonate, nicotinate, 2-naphthalenesulfonate, oxalate, palmoate, pectinate, persulfate, 3-phenylproprionate, picrate, pivalate, propionate, succinate, tartrate, trichloroacetate, trifluoroacetate, phosphate, glutamate, bicarbonate, para-toluenesulfonate, and undecanoate. Examples of acids which can be employed to form pharmaceutically acceptable addition salts include inorganic acids such as hydrochloric, hydrobromic, sulfuric, and phosphoric, and organic acids such as oxalic, maleic, succinic, and citric.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of pharmaceutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, and N,N'-dibenzylethylenediamine. Other representative organic amines useful for the formation of base addition salts include ethylenediamine, ethanolamine, diethanolamine, piperidine, and piperazine.

When it is possible that, for use in therapy, therapeutically effective amounts of a compound of Formula (I), as well as pharmaceutically acceptable salts thereof, may be administered as the raw chemical, it is possible to present the active ingredient as a pharmaceutical composition. Accordingly, the disclosure further provides pharmaceutical compositions, which include therapeutically effective amounts of compounds of Formula (I) or pharmaceutically acceptable salts thereof, and one or more pharmaceutically acceptable carriers, diluents, or excipients. The term "therapeutically effective amount," as used herein, refers to the total amount of each active component that is sufficient to show a meaningful patient benefit. When applied to an individual active ingredient, administered alone, the term refers to that ingredient alone. When applied to a combination, the term refers to combined amounts of the active ingredients that result in the therapeutic effect, whether administered in combination, serially, or simultaneously. The compounds of Formula (I) and pharmaceutically acceptable salts thereof, are as described above. The carrier(s), diluent(s), or excipient(s) must be acceptable in the sense of being compatible with the other ingredients of the formulation and not deleterious to the recipient thereof. In accordance with another aspect of the present disclosure there is also provided a process for the preparation of a pharmaceutical formulation including admixing a compound of Formula (I), or a pharmaceutically acceptable salt thereof, with one or more pharmaceutically acceptable carriers, diluents, or excipients. The term "pharmaceutically acceptable," as used herein, refers to those compounds, materials, compositions, and/or dosage forms which are, within the scope of sound medical judgment, suitable for use in contact with the tissues of patients without excessive toxicity, irritation, allergic response, or other problem or complication commensurate with a reasonable benefit/risk ratio, and are effective for their intended use.

Pharmaceutical formulations may be presented in unit dose forms containing a predetermined amount of active ingredient per unit dose. Dosage levels of between about 0.01 and about 250 milligram per kilogram ("mg/kg") body weight per day, preferably between about 0.05 and about 100 mg/kg body weight per day of the compounds of the present disclosure are typical in a monotherapy for the prevention and treatment of disease. Typically, the pharmaceutical compositions of this disclosure will be administered from about 1 to about 5 times per day or alternatively, as a continuous infusion. Such administration can be used as a chronic or acute therapy. The amount of active ingredient that may be combined with the carrier materials to produce a single dosage form will vary depending on the condition being treated, the severity of the condition, the time of administration, the route of administration, the rate of excretion of the compound employed, the duration of treatment, and the age, gender, weight, and condition of the patient. Preferred unit dosage formulations are those containing a daily dose or sub-dose, as herein above recited, or an appropriate fraction thereof, of an active ingredient. Treatment may be initiated with small dosages substantially less than the optimum dose of the compound. Thereafter, the dosage is increased by small increments until the optimum effect under the circumstances is reached. In general, the compound is most desirably administered at a concentration level that will generally afford effective results without causing any harmful or deleterious side effects.

When the compositions of this disclosure comprise a combination of a compound of the present disclosure and one or more additional therapeutic or prophylactic agent, both the compound and the additional agent are usually present at dosage levels of between about 10 to 150%, and more preferably between about 10 and 80% of the dosage normally administered in a monotherapy regimen.

Pharmaceutical formulations may be adapted for administration by any appropriate route, for example by the oral (including buccal or sublingual), rectal, nasal, topical (including buccal, sublingual, or transdermal), vaginal, or parenteral (including subcutaneous, intracutaneous, intramuscular, intra-articular, intrasynovial, intrasternal, intrathecal, intralesional, intravenous, or intradermal injections or infusions) route. Such formulations may be prepared by any method known in the art of pharmacy, for example by bringing into association the active ingredient with the carrier(s) or excipient(s). Oral administration or administration by injection are preferred.

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil emulsions.

For instance, for oral administration in the form of a tablet or capsule, the active drug component can be combined with an oral, non-toxic pharmaceutically acceptable inert carrier such as ethanol, glycerol, water, and the like. Powders are prepared by comminuting the compound to a suitable fine size and mixing with a similarly comminuted pharmaceutical carrier such as an edible carbohydrate, as, for example, starch or mannitol. Flavoring, preservative, dispersing, and coloring agent can also be present.

Capsules are made by preparing a powder mixture, as described above, and filling formed gelatin sheaths. Glidants and lubricants such as colloidal silica, talc, magnesium stearate, calcium stearate, or solid polyethylene glycol can be added to the powder mixture before the filling operation. A disintegrating or solubilizing agent such as agar-agar, calcium carbonate, or sodium carbonate can also be added to improve the availability of the medicament when the capsule is ingested.

Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, and the like. Lubricants used in these dosage forms include sodium oleate, sodium chloride, and the like. Disintegrators include, without limitation, starch, methyl cellulose, agar, betonite, xanthan gum, and the like. Tablets are formulated, for example, by preparing a powder mixture, granulating or slugging, adding a lubricant and disintegrant, and pressing into tablets. A powder mixture is prepared by mixing the compound, suitable comminuted, with a diluent or base as described above, and optionally, with a binder such as carboxymethylcellulose, an aliginate, gelating, or polyvinyl pyrrolidone, a solution retardant such as paraffin, a resorption accelerator such as a quaternary salt and/or and absorption agent such as betonite, kaolin, or dicalcium phosphate. The powder mixture can be granulated by wetting with a binder such as syrup, starch paste, acadia mucilage, or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc, or mineral oil. The lubricated mixture is then compressed into tablets. The compounds of the present disclosure can also be combined with a free flowing inert carrier and compressed into tablets directly without going through the granulating or slugging steps. A clear or opaque protective coating consisting of a sealing coat of shellac, a coating of sugar or polymeric material, and a polish coating of wax can be provided. Dyestuffs can be added to these coatings to distinguish different unit dosages.

Oral fluids such as solution, syrups, and elixirs can be prepared in dosage unit form so that a given quantity contains a predetermined amount of the compound. Syrups can be prepared by dissolving the compound in a suitably flavored aqueous solution, while elixirs are prepared through the use of a non-toxic vehicle. Solubilizers and emulsifiers such as ethoxylated isostearyl alcohols and polyoxyethylene sorbitol ethers, preservatives, flavor additive such as peppermint oil or natural sweeteners, or saccharin or other artificial sweeteners, and the like can also be added.

Where appropriate, dosage unit formulations for oral administration can be microencapsulated. The formulation can also be prepared to prolong or sustain the release as for example by coating or embedding particulate material in polymers, wax, or the like.

The compounds of Formula (I), and pharmaceutically acceptable salts thereof, can also be administered in the form of liposome delivery systems, such as small unilamellar vesicles, large unilamellar vesicles, and multilamellar vesicles. Liposomes can be formed from a variety of phopholipids, such as cholesterol, stearylamine, or phophatidylcholines.

The compounds of Formula (I) and pharmaceutically acceptable salts thereof may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxide-polylysine substituted with palitoyl residues. Furthermore, the compounds may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates, and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in *Pharmaceutical Research* 1986, 3(6), 318.

Pharmaceutical formulations adapted for topical administration may be formulated as ointments, creams, suspensions, lotions, powders, solutions, pastes, gels, sprays, aerosols, or oils.

Pharmaceutical formulations adapted for rectal administration may be presented as suppositories or as enemas.

Pharmaceutical formulations adapted for nasal administration wherein the carrier is a solid include a course powder having a particle size for example in the range 20 to 500 microns which is administered in the manner in which snuff is taken, i.e., by rapid inhalation through the nasal passage from a container of the powder held close up to the nose. Suitable formulations wherein the carrier is a liquid, for administration as a nasal spray or nasal drops, include aqueous or oil solutions of the active ingredient.

Pharmaceutical formulations adapted for administration by inhalation include fine particle dusts or mists, which may be generated by means of various types of metered, dose pressurized aerosols, nebulizers, or insufflators.

Pharmaceutical formulations adapted for vaginal administration may be presented as pessaries, tampons, creams, gels, pastes, foams, or spray formulations.

Pharmaceutical formulations adapted for parenteral administration include aqueous and non-aqueous sterile injection solutions which may contain anti-oxidants, buffers, bacteriostats, and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets.

It should be understood that in addition to the ingredients particularly mentioned above, the formulations may include other agents conventional in the art having regard to the type of formulation in question, for example those suitable for oral administration may include flavoring agents.

The term "patient" includes both human and other mammals.

The term "treating" refers to: (i) preventing a disease, disorder or condition from occurring in a patient that may be predisposed to the disease, disorder, and/or condition but has not yet been diagnosed as having it; (ii) inhibiting the disease, disorder, or condition, i.e., arresting its development; and (iii) relieving the disease, disorder, or condition, i.e., causing regression of the disease, disorder, and/or condition.

This disclosure is intended to encompass compounds having Formula (I) when prepared by synthetic processes or by metabolic processes including those occurring in the human or animal body (in vivo) or processes occurring in vitro.

The abbreviations used in the present application, including particularly in the illustrative schemes and examples which follow, are well-known to those skilled in the art. Some of the abbreviations used are as follows: HATU for O-(7-azabenzotriazol-1-yl)-N,N,N',N'-tetramethyluronium hexafluorophosphate; BOP for benzotriazol-1-yloxytris(dimethylamino)phosphonium hexafluorophosphate; EDC or EDCI for 1-(3-dimethylaminopropyl)-3-ethylcarbodiimide hydrochloride; TBTU for O-benzotriazol-1-yl-N,N,N',N'-tetramethyluronium tetrafluoroborate; DCM for dichloromethane; AcO or OAc for acetate; MeOH for methanol; iPr for isopropyl; DMF for N,N-dimethylformamide; Me for methyl; Et for ethyl; Ar for aryl; Bn for benzyl; Ph for phenyl; Cbz for carbobenzyloxy; TBS for tert-butyldimethylsilyl; PG for protecting group; Boc or BOC for tert-butoxycarbonyl; DIAD for diisopropyl azodicarboxylate; TEA or Et₃N for triethylamine; DME for 1,2-dimethoxyethane; LAH for lithium aluminum hydride; THF for tetrahydrofuran; TFA for trifluoracetic acid; EtOH for ethanol; RT or rt for room temperature; min or mins for minutes; h or hr for hours; (DHQD)₂PHAL for hydroquinidine 1,4-phthalazinediyl diether; EtOAc for ethyl acetate; iPrOH for isopropyl alcohol; nBuLi for n-butyllithium; hex for hexanes; ᵗBuO for tert-butoxy; n-PrOH for n-propanol; HOAt for 1-Hydroxy-7-azabenzotriazole; TBAF for tetrabutylammonium fluoride; and DIEA for diisopropylethylamine

EXAMPLES

The present disclosure will now be described in connection with certain embodiments which are not intended to limit its scope. On the contrary, the present disclosure covers all alternatives, modifications, and equivalents as can be included within the scope of the claims. Thus, the following examples, which include specific embodiments, will illustrate one practice of the present disclosure, it being understood that the examples are for the purposes of illustration of certain embodiments and are presented to provide what is believed to be the most useful and readily understood description of its procedures and conceptual aspects.

The compounds of the present disclosure may be prepared using the reactions and techniques described in this section as well as other synthetic methods known to those of ordinary skill in the art. The reactions are performed in solvents appropriate to the reagents and materials employed and suitable for the transformation being effected. Also, in the description of the synthetic methods described below, it is to be understood that all proposed reaction conditions, including choice of solvents, reaction temperature, duration of the experiment and workup procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents which are compatible with the reaction conditions will be readily apparent to one skilled in the art and alternate methods must then be used.

Compounds of formula 4 are prepared by the methods outlined in Scheme 1. The amine of a compound of formula 1 is coupled with a carboxylic acid, such as compound 2, via the corresponding acyl chloride or using standard peptide coupling reagents such as HATU, BOP, EDC, TBTU, in the presence of a base, such as N,N-diisopropylethylamine, and a solvent, such as dichloromethane (DCM) to produce 3. Suzuki coupling of 3 with an appropriate boronic acid [R₁B(OH)₂] affords compounds of formula 4.

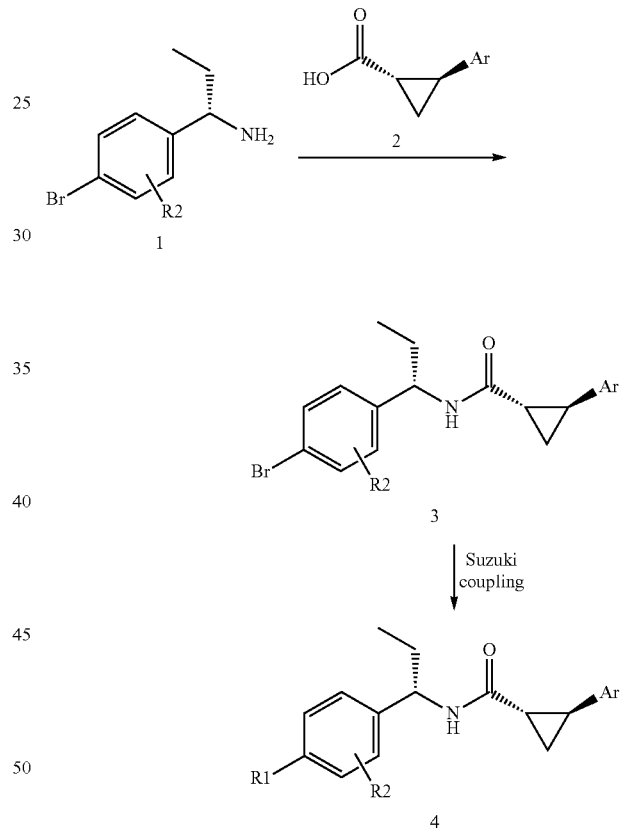

The aryl cyclopropanecarboxylic acids 2 that are not commercially available were prepared according to Scheme 2. The trans-acrylic acid 5 is converted to its corresponding acyl chloride. The acyl chloride is reacted with (+)-L-2,10-camphorsultam 6 to provided intermediate 7. The cyclopropanation 7 with diazomethane, generated from N-methyl nitrosourea 8 under basic conditions, in the presents of Pd(OAc)₂ affords intermediate 9. Compound 9 is treated with Ti(iPrO)₄ in benzyl alcohol to provide intermediate 10. Hydrolysis of 10 with aqueous NaOH in MeOH affords the desired aryl cyclopropanecarboxylic acid 2.

Scheme 2

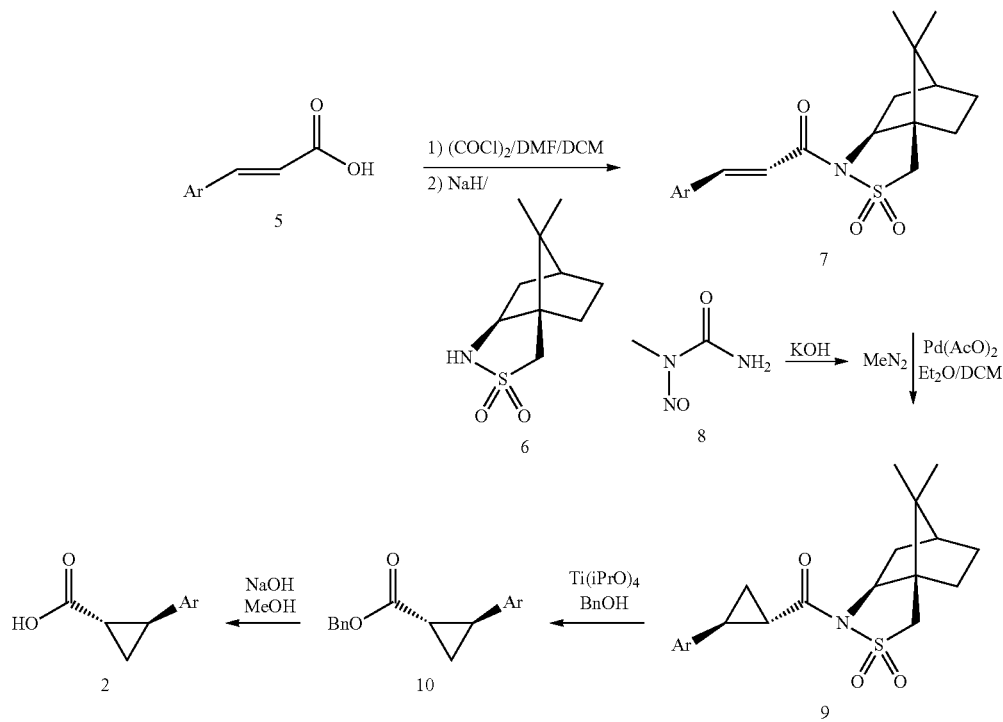

Compounds of formula 15 are prepared by the methods outlined in Scheme 3 or Scheme 4 Aminohydroxylation of compound 11 according to the literature (*JACS*, 1998, 1207-1217) provides intermediate 12. The protecting group of compound 12 is removed under acidic conditions or hydrogenation to afforded compound 13. The amino compound of 13 is coupled with a carboxylic acid, such as compound 2, via the corresponding acyl chloride or using standard peptide coupling reagents such as HATU, BOP, EDC, TBTU, in the presence of a base, such as N,N-diisopropylethylamine, and a solvent, such as dichloromethane (DCM) to produce 14. Suzuki coupling of 14 with an appropriate boronic acid [$R_1B(OH)_2$] affords compounds of formula 15.

Scheme 3

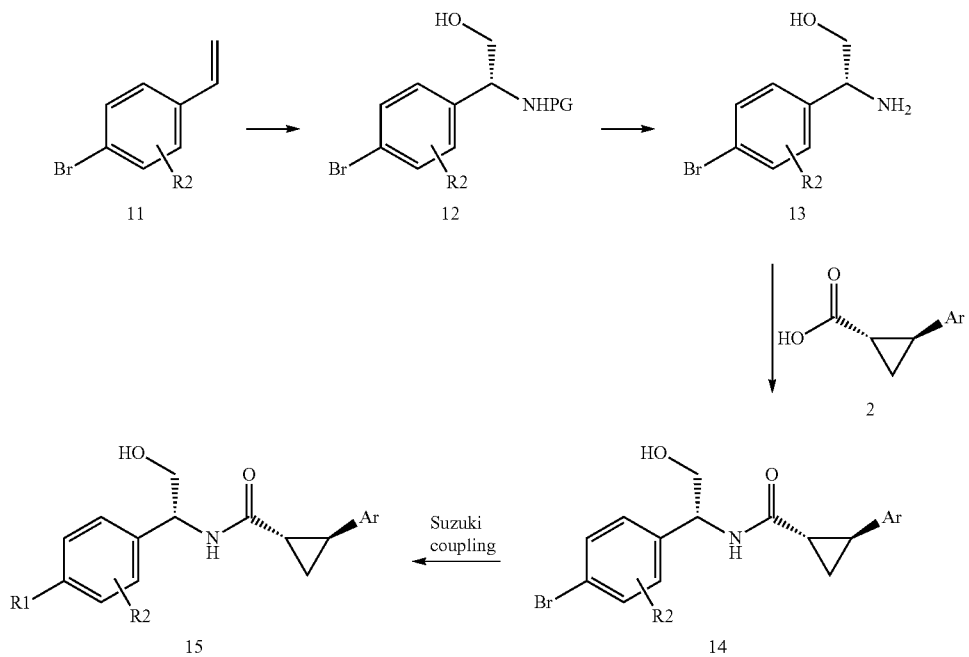

Aminohydroxylation of compound 16 according to the literature (*JACS*, 1998, 1207-1217) provides intermediate 17. Both benzyl and benzyl carbamate protecting group are removed by hydrogenation. The amine is protected again as benzyl carbamate and the phenol is protected as a silyl ether to afford compound 19. The benzyl carbamate of compound 19 is removed by hydrogenation to afforded compound 20. The amino compound of 20 is coupled with a carboxylic acid, such as compound 2, via the corresponding acyl chloride or using standard peptide coupling reagents such as HATU, BOP, EDC, TBTU, in the presence of a base, such as N,N-diisopropylethylamine, and a solvent, such as dichloromethane (DCM) to produce 21. Removal of the silyl protecting group provides compound 22. Compound 22 is then converted to the corresponding triflate 23 by reacting with a triflating reagent. Catalytic coupling of 23 with an appropriate boronic acid [$R_1B(OH)_2$] or other agent such as alkyne affords compounds of formula 15.

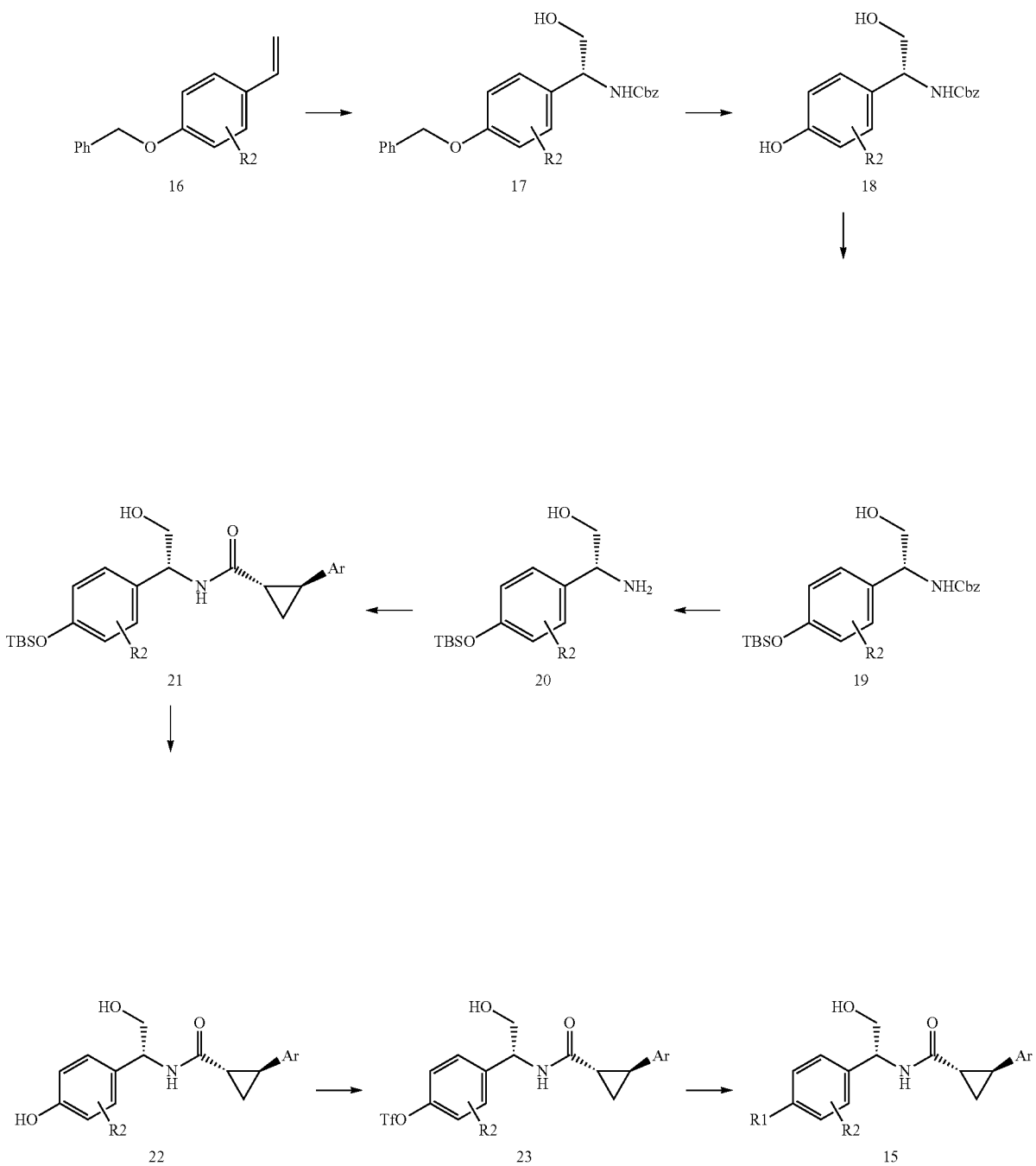

Scheme 4

Compounds of formula 29 are prepared by the methods outlined in Scheme 5. Aminohydroxylation of compound 24 according to the literature (*JACS,* 1998, 1207-1217) provides intermediate 25. The amino protecting group of compound 25 is removed by hydrogenation or under acidic conditions to afford compound 26. The amino compound of 26 is coupled with a carboxylic acid, such as compound 2, via the corresponding acyl chloride or using standard peptide coupling reagents such as HATU, BOP, EDC, TBTU, in the presence of a base, such as N,N-diisopropylethylamine, and a solvent, such as dichloromethane (DCM) to produce 27. The phenol protecting group of compound 27 is removed to provide the phenol compound 28. Alkylation of compound 28 with an appropriate alkylating agent under basic conditions affords compounds of formula 29. Alternatively, the phenol protecting group of compound 25 is removed first to afford the phenol compound 30. Alkylation of compound 30 with an appropriate alkylating agent under basic conditions affords compounds 31. The amino protecting group of compound 31 is then removed by hydrogenation or under acidic conditions to afforded compound 32. The amino compound of 32 is coupled with a carboxylic acid, such as compound 2, via the corresponding acyl chloride or using standard peptide coupling reagents such as HATU, BOP, EDC, TBTU, in the presence of a base, such as N,N-diisopropylethylamine, and a solvent, such as dichloromethane (DCM) to produce compounds of formula 29.

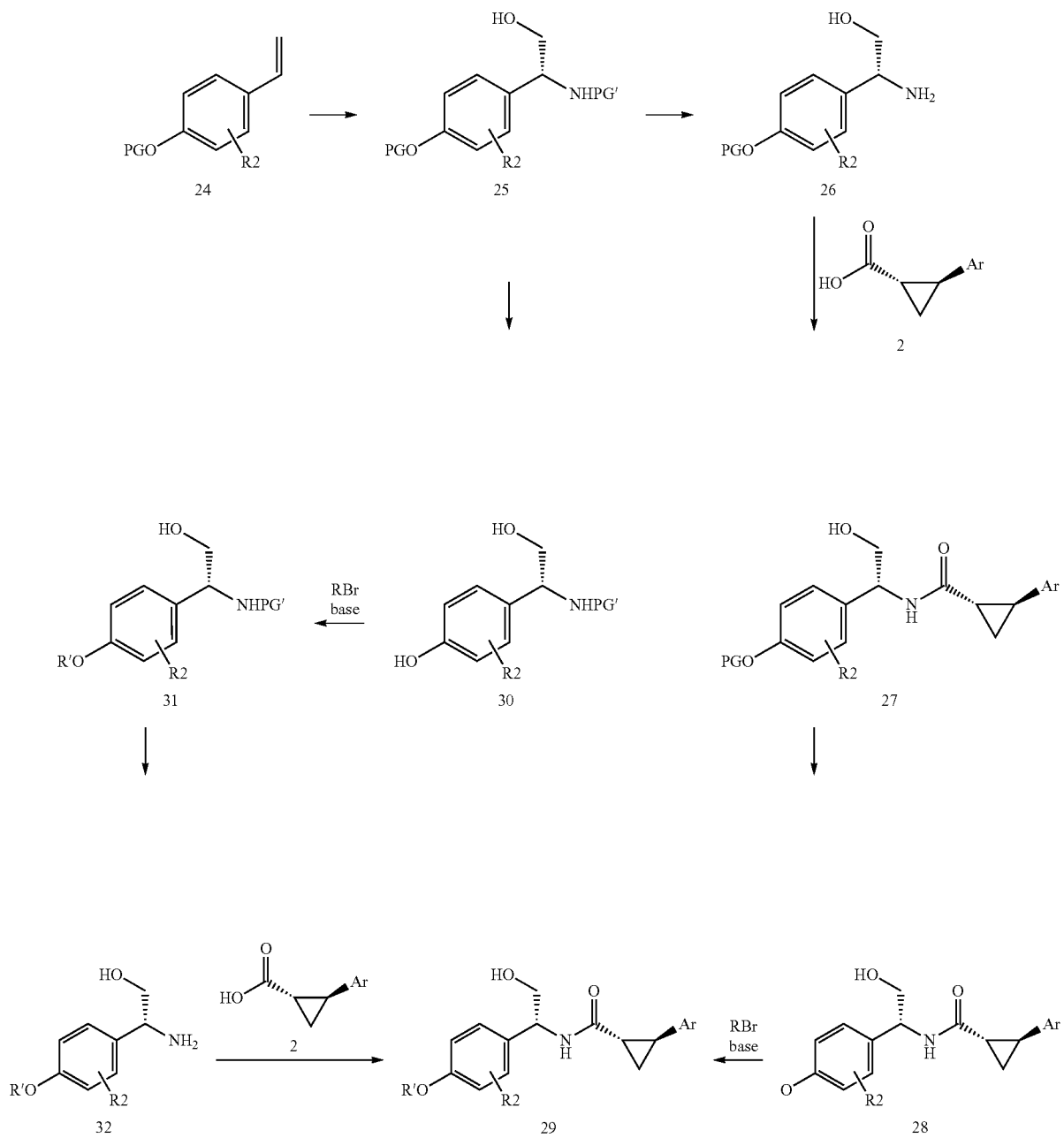

Scheme 5

Compounds of formula 37 are prepared by the methods outlined in Scheme 6. The N-Boc protected amino acid 33 is coupled with N-methyl piperazine using standard peptide coupling reagents such as HATU, BOP, EDC, TBTU, in the presence of a base, such as N,N-diisopropylethylamine, and a solvent, to produce amide 34. The amino protecting group of compound 34 is removed under acidic conditions to provide compound 35. Treatment of the compound 35 with lithium aluminum hydride reduces the amide function to give compound 36. The amine of a compound of 36 is coupled with a carboxylic acid, such as compound 2, via the corresponding acyl chloride or using standard peptide coupling reagents such as HATU, BOP, EDC, TBTU, in the presence of a base, such as N,N-diisopropylethylamine, and a solvent, such as dichloromethane (DCM) to produce compounds of formula 37.

Scheme 6

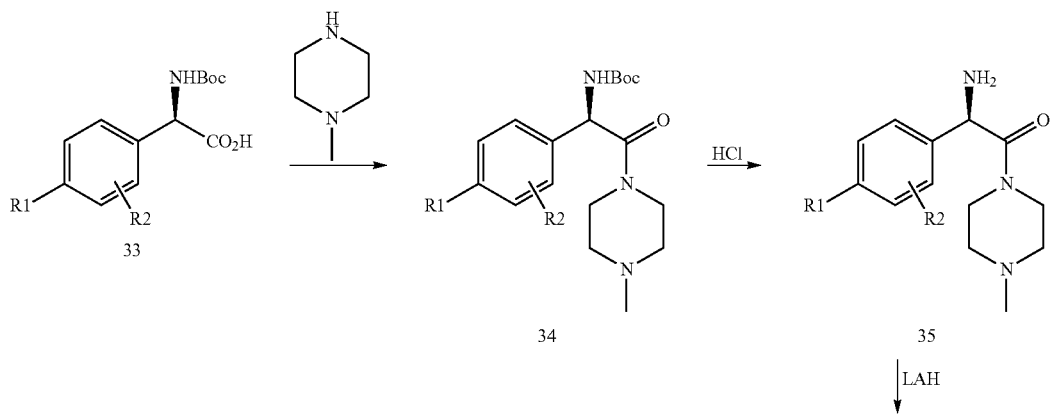

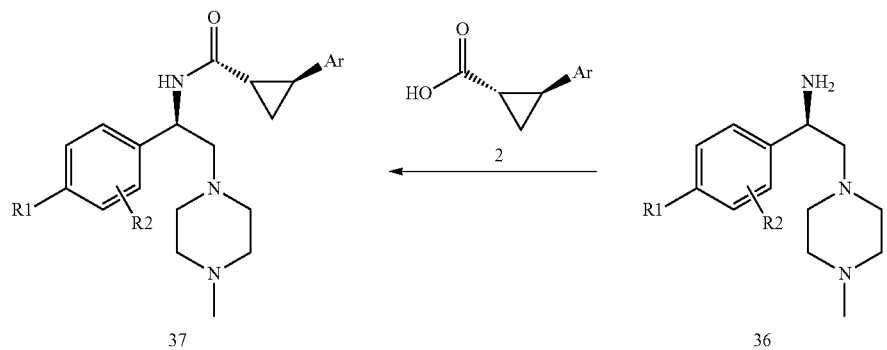

Compounds of formula 45 are prepared by the methods outlined in Scheme 7. The amine group in compound 38 is protected as t-butyl carbamate to afford compound 39. Then the phenol group in compound 39 is protected as a silyl ether to give compound 40. Compound 40 is coupled with N-methyl piperazine using standard peptide coupling reagents such as HATU, BOP, EDC, TBTU, in the presence of a base, such as N,N-diisopropylethylamine, and a solvent, to produce amide 41. Reduction of the amide function in compound 41 gives compound 42. Treatment of compound 42 with tetrabutyl ammonium fluoride removes the silyl group to provide compound 43. Alkylation of compound 43 with an appropriate alkylating agent under basic conditions affords compounds 44. Removal of the t-butyl carbamate group under acidic conditions followed by coupling with a carboxylic acid, such as compound 2, via the corresponding acyl chloride or using standard peptide coupling reagents such as HATU, BOP, EDC, TBTU, in the presence of a base, such as N,N-diisopropylethylamine, and a solvent, such as dichloromethane (DCM) produce compounds of formula 45.

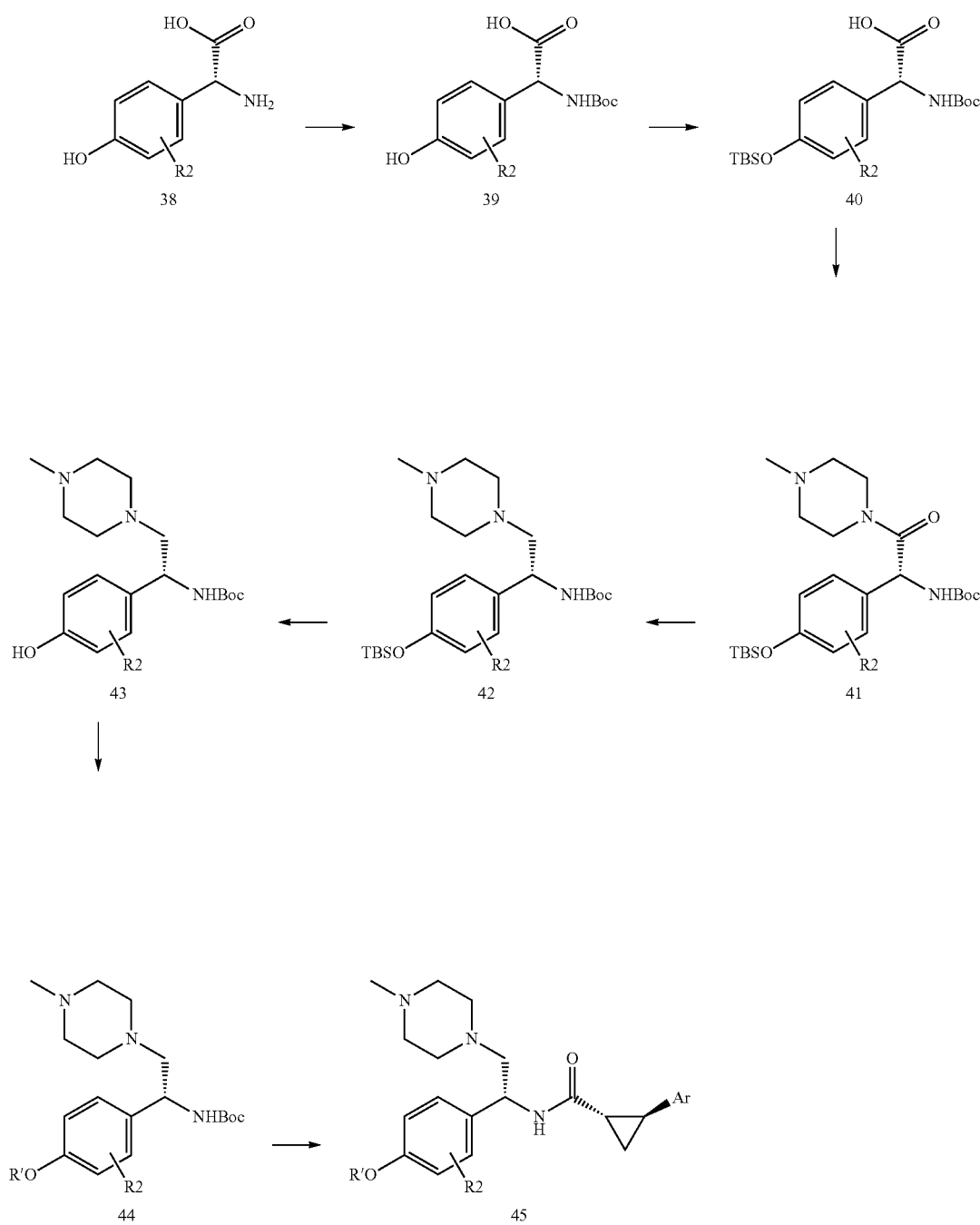

Scheme 7

Compounds of formula 47 are prepared by the methods outlined in Scheme 8. Mitsunobu reaction of compound 15 with phthalimide provides compound 46. Treatment of compound 46 with hydrazine gives compound 47.

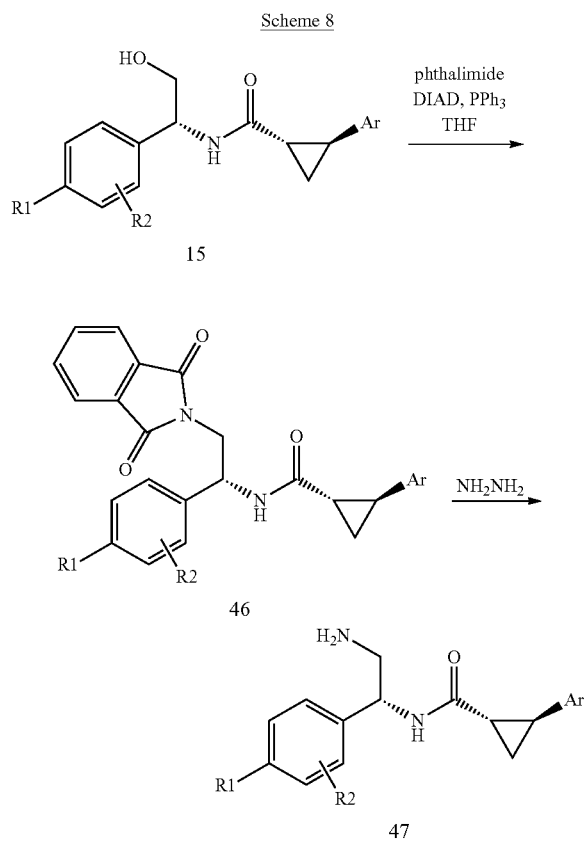

Compounds of formula 54 are prepared by the methods outlined in Scheme 9. The amine of a compound of formula 48 is protected with an appropriate protecting group reagent as described in *Protective Groups in Organic Synthesis* (Greene, Wuts; 3$^{rd}$ ed., 1999, John Wiley & Sons, Inc.), preferably t-butylcarbamate. The reaction is carried out in the presence of an appropriate base, such as N,N-diisopropylethylamine to produce the boc-protected compound 49. Alkylation of the hydroxyl group in 49 is achieved by treatment of 49 with an alcohol (R'OH), triphenylphosphine, an azodicarboxylate ester $R^cO_2CN=NCO_2R^c$ (where $R^c$ is lower alkyl) in an inert solvent, such as tetrahydrofuran or methylene chloride, at temperatures ranging from 0° C. to 150° C. The choices of phosphine, solvent or azodicarboxylate ester are known to those skilled in the art of organic chemistry as described by Mitsunobu (Mitsunobu, O. *Synthesis* 1981, 1). Reduction of the ester in 50 is carried out in the presence of a reducing agent such as lithium aluminum hydride, lithium borohydride or sodium borohydride in the presence of lithium chloride in a mixture of tetrahydrofuran and ethanol to furnish intermediate 51. Mitsunobu reaction of compound 51 with phthalimide provided compound 52. Removal of the t-butyl carbamate group under acidic conditions followed by coupling with a carboxylic acid, such as compound 2, via the corresponding acyl chloride or using standard peptide coupling reagents such as HATU, BOP, EDC, TBTU, in the presence of a base, such as N,N-diisopropylethylamine, and a solvent, such as dichloromethane (DCM) produce compounds 53. Treatment of compound 53 with hydrazine gives compound of formula 54.

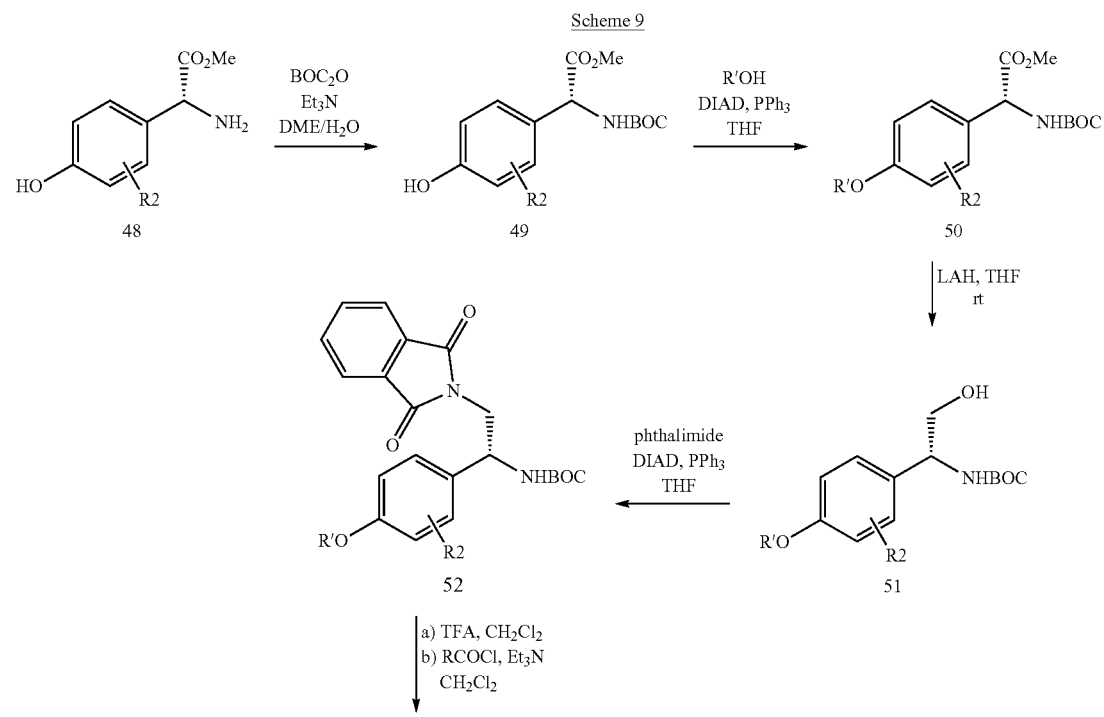

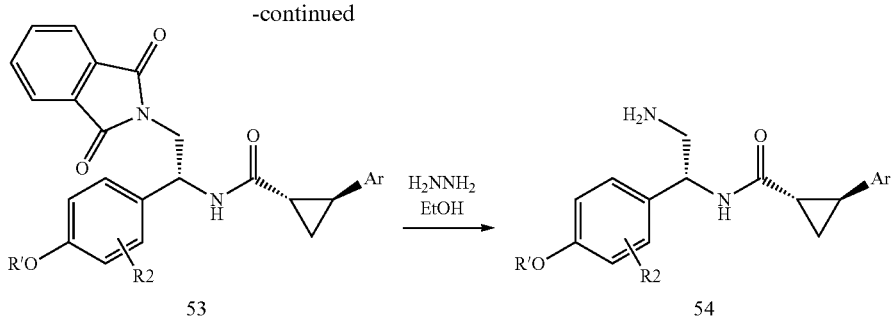

Various analogs synthesized using Schemes 1-9 are listed in Table 1.

TABLE 1

(I)

| Example | R¹ | R² | Ar | X | (M + H)⁺ |
|---|---|---|---|---|---|
| 1 | 4-methoxyphenyl | H | Ph | Me | 386.2 |
| 2 | 4-methylphenyl | H | 2-thiophenyl | OH | 378 |
| 3 | 2-ethylbutoxy | 2-MeO | Ph | OH | 412 |
| 4 | 4-ethylphenyl | H | 2-thiophenyl | OH | 392 |
| 5 | 4-methylphenyl | H | 2-thiophenyl | OH | 378 |
| 6 | (S)-2-methylbutoxy | H | 2-thiophenyl | OH | 374.3 |
| 7 | 2-ethylbutoxy | H | 2-thiophenyl | OH | 388 |
| 8 | 2-ethylbutoxy | 2-Me | 2-thiophenyl | OH | 402 |
| 9 | (S)-2-methylbutoxy | 2-Me | 2-thiophenyl | OH | 388.3 |
| 10 | 2-methylpentoxy | 2-Me | 2-thiophenyl | OH | 402 |
| 11 | 2-methylpentoxy | H | 2-thiophenyl | 4-methyl-piperazine | 470 |
| 12 | 4-methylphenyl | 2-MeO | 2-thiophenyl | OH | 408 |
| 13 | 4-ethylphenyl | 2-MeO | 2-thiophenyl | OH | 422.2 |
| 14 | 1-pentynyl | 2-MeO | 2-thiophenyl | OH | 384 |
| 15 | 2-methylpentoxy | H | 2-thiophenyl | OH | 388.2 |
| 16 | (S)-2-methylbutoxy | H | 2-thiophenyl | 4-methyl-piperazine | 456.3 |
| 17 | (S)-2-methylbutoxy | H | 2-thiophenyl | NH₂ | 373.2 |
| 18 | (S)-2-methylbutoxy | Me | 2-thiophenyl | NH₂ | 387.2 |

In the following examples, all temperatures are given in degrees Centigrade. Melting points were recorded on a Meltemp 3.0 Laboratory Devices, Inc. capillary melting point apparatus and are uncorrected. Proton magnetic resonance (¹H NMR) spectra were recorded on a Bruker Avance 300, a Bruker Avance 400, or a Bruker Avance 500 spectrometer. All spectra were determined in the solvents indicated and chemical shifts are reported in δ units downfield from the internal standard tetramethylsilane (TMS) and interproton coupling constants are reported in Hertz (Hz). Multiplicity patterns are designated as follows: s, singlet; d, doublet; t, triplet; q, quartet; m, multiplet; br, broad peak; dd, doublet of doublet; br d, broad doublet; dt, doublet of triplet; br s, broad singlet; dq, doublet of quartet Infrared (IR) spectra using potassium bromide (KBr) or sodium chloride film were determined on a Jasco FT/IR-410 or a Perkin Elmer 2000 FT-IR spectrometer from 4000 cm⁻¹ to 400 cm⁻¹, calibrated to 1601 cm⁻¹ absorption of a polystyrene film and reported in reciprocal centimeters (cm⁻¹). Optical rotations $[\alpha]_D$ were determined on a Rudolph Scientific Autopol IV polarimeter in the solvents indicated; concentrations are given in mg/mL. Low resolution mass spectra (MS) and the apparent molecular (MH⁺) or (M−H)⁺ was determined on a Finnegan SSQ7000. High resolution mass spectra were determined on a Finnegan MAT900. Liquid chromatography (LC)/mass spectra were run on a Shimadzu LC coupled to a Water Micromass ZQ.

Example 1

(1S,2S)-2-phenyl-cyclopropanecarboxylic acid [(S)-1-(4'-methoxy-biphenyl-4-yl)-propyl]-amide

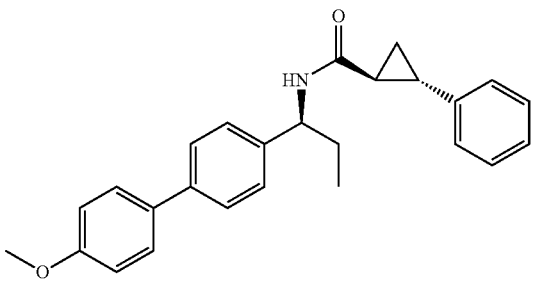 [SMILES: CC[C@H](NC(=O)[C@H]1C[C@@H]1c1ccccc1)c1ccc(-c2ccc(OC)cc2)cc1]

Part A. (1S,2S)-2-phenyl-cyclopropanecarboxylic acid [(S)-1-(4-bromo-phenyl)-propyl]-amide To a solution of (1S,2S)-2-phenyl-cyclopropanecarboxylic acid (170 mg, 1.05 mmol) in dichloromethane (10 ml) was added oxalyl dichloride (145 mg, 1.2 mmol) followed by a few drops of N,N-dimethylformamide at RT. The reaction mixture was stirred at RT for 45 mins before it was concentrated down and dissolved in dichloromethane (1.5 ml). The solution was added slowly to a solution of (S)-1-(4-bromo-phenyl)-propylamine (250 mg, 1.0 mmol, HCl salt) and triethylamine (222 mg, 2.2 mmol) in dichloromethane (10 ml)

at 0° C. The resulting reaction mixture was stirred at RT for 1.5 h. Water was added and the aqueous layer was extracted by dichloromethane. Organic layer was dried by magnesium sulfate and concentrated. The residue was purified via column chromatography on silica gel to afford (1S,2S)-2-phenyl-cyclopropanecarboxylic acid [(S)-1-(4-bromo-phenyl)-propyl]-amide (330 mg, 92%). $^1$H NMR (400 MHz, CHLOROFORM-d) δ ppm 7.37 (d, J=8.6 Hz, 2H), 7.15-7.23 (m, 2H), 7.11 (d, J=7.3 Hz, 1H), 7.08 (d, J=8.3 Hz, 2H), 6.98 (d, J=7.3 Hz, 2H), 5.75 (d, J=7.6 Hz, 1H), 4.77 (q, J=7.5 Hz, 1H), 2.31-2.41 (m, 1H), 1.65-1.81 (m, 2H), 1.48-1.59 (m, 2H), 1.12-1.23 (m, 1H), 0.82 (t, J=7.4 Hz, 3H); LRMS (ESI) (M+1)=360.04. Molecular Formula=$C_{19}H_{20}BrNO$.

Part B. (1S,2S)-2-phenyl-cyclopropanecarboxylic acid [(S)-1-(4'-methoxy-biphenyl-4-yl)-ropyl]-amide A suspension of (1S,2S)-2-phenyl-cyclopropanecarboxylic acid [(S)-1-(4-bromo-phenyl)-propyl]-amide (60 mg, 0.17 mmol), 4-methoxyphenylboronic acid (51 mg, 0.34 mmol), [1,1'-bis(diphenylphosphino)ferrocene]dichloropalladium (II), complex with dichloromethane (1:1) (13 mg, 0.017 mmol) and potassium phosphate (72 mg, 0.34 mmol) in dimethoxyethane (2 ml) and water (0.6 ml) was subjected to microwave heating at 160° C. for 5 mins. The reaction mixture was washed by sodium hydroxide (1N, aqueous solution) before it was extracted with ethyl acetate. Organic layer was dried by magnesium sulfate and concentrated. The residue was purified via column chromatography on silica gel to afford (1S,2S)-2-phenyl-cyclopropanecarboxylic acid [(S)-1-(4'-methoxy-biphenyl-4-yl)-ropyl]-amide (20.4 mg, 31% yield). $^1$H NMR (400 MHz, CHLOROFORM-d) δ ppm 7.43 (dd, J=8.3, 2.8 Hz, 4H), 7.25 (d, J=8.1 Hz, 2H), 7.17 (d, J=7.8 Hz, 2H), 7.06-7.13 (m, 1H), 6.99 (d, J=7.3 Hz, 2H), 6.89 (d, J=8.6 Hz, 2H), 5.76 (d, J=7.6 Hz, 1H), 4.81-4.92 (m, 1H), 2.35-2.45 (m, 1H), 1.73-1.89 (m, 2H), 1.51-1.62 (m, 2H), 1.19 (br. s., 2H), 1.12-1.25 (m, 2H), 0.86 (t, J=7.3 Hz, 3H); LRMS (ESI)=386.2, [(M+1)$^+$ calcd for $C_{26}H_{28}NO_2$ 386.5].

Example 2

(1R,2R)-2-Thiophen-2-yl-cyclopropanecarboxylic acid [(R)-2-hydroxy-1-(4'-methyl-biphenyl-4-yl)-ethyl]-amide

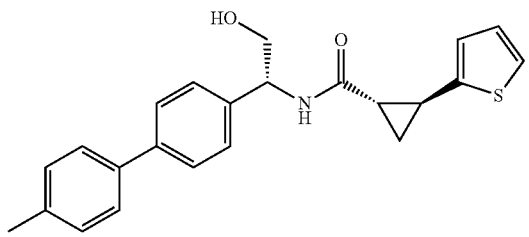 [SMILES: Cc1ccc(-c2ccc([C@H](CO)NC(=O)[C@H]3C[C@@H]3c3cccs3)cc2)cc1]

Part A. [(R)-1-(4-Bromo-phenyl)-2-hydroxy-ethyl]-carbamic acid tert-butyl ester

To a solution of t-butyl carbamate (1.82 g, 15.5 mmol) in n-propanol (20 ml) was added the solution of sodium hydroxide (1N, 15.25 mol), then added freshly made t-butyl hypochloride (1.75 ml, 15.25 mmol). The mixture was stirred for 5 minutes at room temperature. This reaction mixture was then placed in an ice-bath, (DHQD)$_2$PHAL (0.234 g, 0.3 mmol) in n-propanol (20 ml) and 1-Bromo-4-vinyl-benzene (915 mg, 5 mmol) in n-propanol (35 ml) were added sequentially, stirred for 6 minutes. $K_2OsO_2 \cdot 2H_2O$ (0.074 g, 0.2 mmol) was added directly at 0° C. The final reaction mixture was stirred for 1.5 hrs to generate a light yellow clear solution. A saturated solution of sodium sulfite (50 ml) was added to quench the reaction at 0° C. Excessive n-propanol was removed in a high vacuum. The aqueous phase was extracted by ethyl acetate (3×30 ml). The combined organic layers were washed with brine (2×30 ml), then dried over MgSO$_4$, filtered and concentrated to give a yellow crude solid. The crude product was purified via column chromatography on silica gel with a gradient of 0%-100% of ethyl acetate in hexanes to afford a white solid (920 mg, 58% yield).

Part B. (R)-2-Amino-2-(4-bromo-phenyl)-ethanol

A solution of [(R)-1-(4-bromo-phenyl)-2-hydroxy-ethyl]-carbamic acid t-butyl ester (946 mg, 3 mmol) in MeOH (15 ml) was treated with HCl in dioxane (4 M, 15 ml) for 1.5 h. The mixture was concentrated to give the titled compound (755 mg, 100%) as a white solid.

Part C. (1S,2S)-2-Thiophen-2-yl-cyclopropanecarboxylic acid [(R)-1-(4-bromo-phenyl)-2-hydroxy-ethyl]-amide To a solution of (1S,2S)-2-thiophen-2-yl-cyclopropanecarboxylic acid (655 mg, 3.9 mmol) in DCM (15 ml) was added oxalyl chloride (2 M in DCM, 2.14 ml) and few drops of DMF. The mixture was stirred for 3 h and then concentrated. The residue was suspended in DCM and concentrated again. The process was repeated twice more.

The above residue (2.5 mmol) was suspended in DCM (2.5 ml). To the suspension was added (R)-2-amino-2-(4-bromo-phenyl)-ethanol (600 mg, 2.38 mmol) and triethyl amine (660 ul, 4.76 mmol). The resulting mixture was stirred at rt for 20 min. The reaction mixture was poured into saturated aqueous NaHCO$_3$ and extracted 3 times with EtOAc. The combined EtOAc layer was dried (MgSO$_4$) and concentrated. The residue was subjected to flash gel silica column (30% EtOAc in DCM) to give the titled compounds (560 mg, 64%).

Part D. (1S,2S)-2-Thiophen-2-yl-cyclopropanecarboxylic acid [(R)-2-hydroxy-1-(4'-methyl-biphenyl-4-yl)-ethyl]-amide A mixture of (1S,2S)-2-thiophen-2-yl-cyclopropanecarboxylic acid [(R)-1-(4-bromo-phenyl)-2-hydroxy-ethyl]-amide (560 mg, 1.53 mmol), K$_3$PO$_4$ (650 mg, 3.0 mmol)) and p-tolylboronic acid (310 mg, 2.3 mmol) in DME/H$_2$O (3/1, 2 ml) was passed through N$_2$ and then Pd(PPh$_3$)$_4$ (178 mg, 0.153 mmol) added. The mixture was stirred in a sealed tube at 85° C. for 1.5 h. The reaction mixture was poured 1N NaOH and extracted with EtOAc (3×). The combined EtOAc layer was dried over MgSO$_4$. After removal of the solvent, the residue was subjected to silica column (50% EtOAc in DCM and then 10% MeOH in DCM). The product obtained was further purified by crystallization (iPrOH/EtOAc) and Prep HPLC to give the titled compound (275 mg). $^1$H NMR (400 MHz, CHLOROFORM-d) δ ppm 7.6 (d, J=8.1 Hz, 2H), 7.5 (d, J=7.8 Hz, 2H), 7.4 (d, J=8.1 Hz, 2H), 7.2 (d, J=7.6 Hz, 2H), 7.1 (t, J=5.4 Hz, 1H), 6.8-7.0 (m, 2H), 5.0 (dd, J=5.4, 1.9 Hz, 1H), 3.7-3.8 (m, 2H), 2.5-2.7 (m, 1H), 2.4 (s, 3H), 2.1 (t, J=8.7

Hz, 1H), 1.4-1.6 (m, 1H), 1.2 (ddd, 1H). LRMS (ESI)=378, [(M+1)+ calcd for $C_{23}H_{24}NO_2S$ 377.5].

Example 3

(1S,2S)-2-Phenyl-cyclopropanecarboxylic acid {(R)-1-[4-(2-ethyl-butoxy)-2-methoxy-phenyl]-2-hydroxy-ethyl}-amide

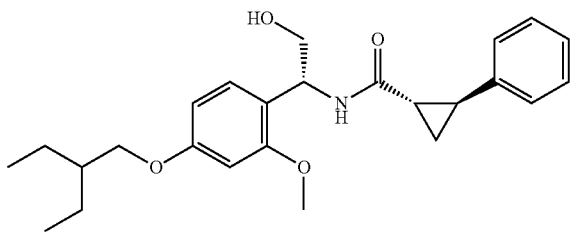 [SMILES: CCC(CC)COc1ccc([C@H](CO)NC(=O)[C@H]2C[C@@H]2c2ccccc2)c(OC)c1]

Part A. 4-Benzyloxy-2-methoxy-1-vinyl-benzene

To a suspension methyltriphenyl-phosphonium bromide (2.66 g, 7.43 mmol) in 60 ml THF at 0° C. was added 4.6 ml (7.43 mmol) of 1.6 M nBuLi. The resulting mixture was stirred at 0° C. for 1 hr, followed by a slow addition of the aldehyde (1.5 g, 6.2 mmol) dissolved in 15 ml THF. The ice bath was removed, and stirred for 2 hr at rt. It was then diluted with ether and quench with water. The organic layer was washed with brine and dried over $MgSO_4$. It was purified in the ISCO using 1-5 EtOAc/hex to obtain 908 mg (61%) of the styrene.

Part B. [(R)-1-(4-Benzyloxy-2-methoxy-phenyl)-2-hydroxy-ethyl]-carbamic acid tert-butyl ester To 569 mg (4.86 mmol) of t-butylcarbamate suspended in 6.3 ml n-propanol was added 4.8 ml 1 N NaOH (4.8 mmol), and freshly prepared tBuOCl (548 ul, 4.8 mmol) and then stirred for 8 min at rt. It was then cooled to 0° C. followed by the addition of the catalyst $(DHQD)_2PHAL$ (73.2 mg, 0.094 mmol) dissolved in 6.3 ml n-PrOH. This was followed by the addition of the styrene (307 mg, 1.28 mmol) also dissolved in 11 ml n-PrOH, and stirred for another 8 min. Then $K_2OsO_4.2H_2O$ (23 mg, 0.063 mmol) was added directly, and the resulting mixture stirred for 1.5 hr at 0° C. Several color changes were observed, from brown, to bright red, to orange and then finally light yellow. Dilute with EtOAc, and quench with aq. $Na_2S_2O_3$. The organic layer was separated and the aqueous layer extracted with EtOAc. The combined organic layers were washed with brine, dried over $MgSO_4$, and concentrated. It was purified on the ISCO using 5-50% EtOAc/hex to obtain 146 mg (30%) of the titled compound.

Part C. [(R)-2-Hydroxy-1-(4-hydroxy-2-methoxy-phenyl)-ethyl]-carbamic acid tert-butyl ester A mixture of [(R)-1-(4-benzyloxy-2-methoxy-phenyl)-2-hydroxy-ethyl]-carbamic acid tert-butyl ester (136 mg, 0.365 mmol) and Pd/C (~10 mg) in MeOH (4 ml) was stirred under $H_2$ (1 atm) for overnight. The mixture was filtered and the filtrate was concentrated to give the titled compound (100 mg, 100%).

Part D. {(R)-1-[4-(2-Ethyl-butoxy)-2-methoxy-phenyl]-2-hydroxy-ethyl}-carbamicacid tert-butyl ester To 34 mg (0.122 mmol) of the [(R)-2-hydroxy-1-(4-hydroxy-2-methoxy-phenyl)-ethyl]-carbamic acid tert-butyl ester and 2-ethylbutylbromide (20 ul, 0.182 mmol) dissolved in 1 ml DMF was added $K_2CO_3$ (34 mg, 0.244 mmol) and heated to 60° C. overnight. It was cooled to rt, diluted with ether, and quenched with water. The organic layer was washed with water and brine, and then dried over $MgSO_4$. After removal of the solvent, the residue was purified by flash column (35% EtOAc in hexane) to give the titled compound (24 mg, 54%).

Part E. (1S,2S)-2-Phenyl-cyclopropanecarboxylic acid {(R)-1-[4-(2-ethyl-butoxy)-2-methoxyphenyl]-2-hydroxy-ethyl}-amide The {(R)-1-[4-(2-Ethyl-butoxy)-2-methoxy-phenyl]-2-hydroxy-ethyl}-carbamicacid tert-butyl ester (24 mg, 0.0654 mmol) was dissolved in 1 mL of MeOH and cooled to 0° C. Then HCl in dioxane (4 M, 330 uL, 1.31 mmol) was slowly added, and the reaction stirred at rt for 4 hr. It was concentrated to obtain the aminoalcohol as HCl salt. It was dissolved in DCM (1 mL) and TEA (20 uL, 0.13 mmol) was added followed by a solution of (1S,2S)-2-phenyl-cyclopropanecarbonyl chloride in DCM (1 M, 0.65 mL, 0.65 mmol, generated as in Example 1). The resulting reaction mixture was stirred at RT for 1.5 h. Water was added and the aqueous layer was extracted by dichloromethane. Organic layer was dried by magnesium sulfate and concentrated. The residue was purified via column chromatography on silica gel to afford the titled compound (9 mg). $^1$H NMR (400 MHz, MeOD) δ ppm 7.0 (t, J=7.5 Hz, 2H), 6.9-7.0 (m, 4H), 6.3 (d, J=2.5 Hz, 1H), 6.3 (dd, J=8.3, 2.3 Hz, 1H), 5.1 (td, J=8.1, 4.8 Hz, 1H), 3.7 (d, J=5.6 Hz, 2H), 3.6 (s, 3H), 3.5 (dd, J=11.2, 4.7 Hz, 1H), 3.4 (dd, J=11.1, 7.8 Hz, 1H), 2.1 (dd, J=6.6, 2.5 Hz, 1H), 1.8 (t, J=8.8 Hz, 1H), 1.4-1.5 (m, 1H), 1.3 (dq, J=14.8, 7.3 Hz, 5H), 1.0 (ddd, J=8.3, 6.3, 4.3 Hz, 1H), 0.7 (t, J=7.6 Hz, 6H). LRMS (ESI)=412, [(M+1)+ calcd for $C_{25}H_{34}NO_4$ 411.5].

Example 4

(1S,2S)-2-Thiophen-2-yl-cyclopropanecarboxylic acid [(R)-1-(4'-ethyl-biphenyl-4-yl)-2-hydroxy-ethyl]-amide

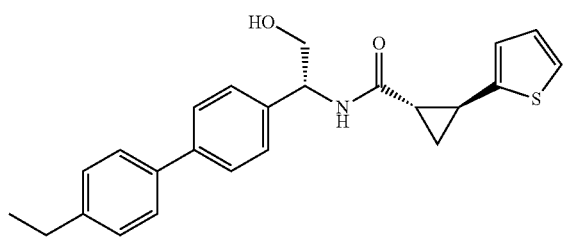 [SMILES: CCc1ccc(-c2ccc([C@H](CO)NC(=O)[C@H]3C[C@@H]3c3cccs3)cc2)cc1]

This example was made same as Example 2 using (1S,2S)-2-thiophen-2-yl-cyclopropanecarboxylic acid and 4-ethylphenylbronic acid. $^1$H NMR (400 MHz, MeOD) δ ppm 7.6 (d, J=8.1 Hz, 2H), 7.5 (d, J=8.3 Hz, 2H), 7.4 (d, J=8.3 Hz, 2H), 7.3 (d, J=8.1 Hz, 2H), 7.2 (d, J=5.3 Hz, 1H), 6.9-7.0 (m, 1H), 6.9 (d, J=3.5 Hz, 1H), 5.1 (t, J=6.4 Hz, 1H), 3.7-3.9 (m, 2H), 2.7 (q, J=7.7 Hz, 2H), 2.5 (dd, J=5.7, 3.9 Hz, 1H), 2.1 (ddd, J=8.7, 4.8, 4.5 Hz, 1H), 1.6 (ddd, J=9.0, 4.8, 4.6 Hz, 1H), 1.3 (t, J=7.6 Hz, 4H). LRMS (ESI)=392, [(M+1)+ calcd for C24H26NO2S 391.5].

Example 5

(1S,2S)-2-Thiophen-2-yl-cyclopropanecarboxylic acid [(R)-2-hydroxy-1-(4'-methyl-biphenyl-4-yl)-ethyl]-amide

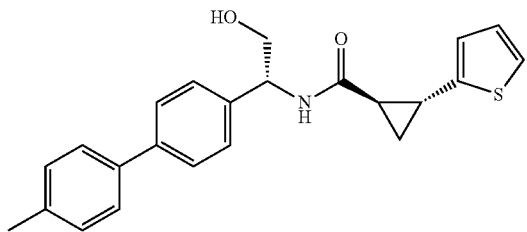 [SMILES: Cc1ccc(-c2ccc([C@H](CO)NC(=O)[C@@H]3C[C@H]3c3cccs3)cc2)cc1]

This example was made same as Example 2 using (1S,2S)-2-thiophen-2-yl-cyclopropanecarboxylic acid. $^1$H NMR (400 MHz, MeOD) δ ppm 7.5 (d, J=8.1 Hz, 2H), 7.4 (d, J=8.1 Hz, 2H), 7.3 (d, J=8.1 Hz, 2H), 7.1 (d, J=7.8 Hz, 2H), 7.0 (d, J=4.5 Hz, 1H), 6.8 (d, J=5.1 Hz, 1H), 6.7 (d, J=3.0 Hz, 1H), 4.9-5.0 (m, 1H), 3.6-3.8 (m, 2H), 2.5 (dd, J=12.9, 6.1 Hz, 1H), 2.3 (s, 3H), 1.8-2.0 (m, 1H), 1.5 (ddd, J=9.1, 4.9, 4.7 Hz, 1H), 1.2 (ddd, 1H). LRMS (ESI)=378, [(M+1)+ calcd for C23H24NO2S 377.5].

Example 6

(1S,2S)-2-Thiophen-2-yl-cyclopropanecarboxylic acid {(R)-2-hydroxy-1-[4-((S)-2-methyl-butoxy)-phenyl]-ethyl}-amide

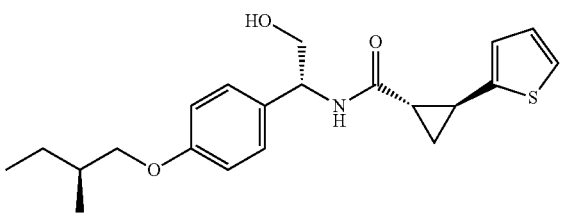 [SMILES: CC[C@H](C)COc1ccc([C@H](CO)NC(=O)[C@H]2C[C@@H]2c2cccs2)cc1]

Part A. (R)-t-Butoxycarbonylamino-(4-hydroxy-phenyl)-acetic acid methyl ester (R)-(−)-2-phenylglycine methyl ester hydrochloride (2.17 g, 10 mmol) and di-t-butyl di-carbonate (2.62 g, 12 mmol) were combined in tetrahydrofuran (100 ml). Triethylamine (1.60 ml, 22 mmol) was added to the mixture via syringe at room temperature. The reaction mixture was stirred at room temperature overnight. The THF in reaction mixture was then removed in vacuum. Saturated aqueous NH4Cl and ethyl acetate were added to the mixture in a separatory funnel. The aqueous layer was extracted with ethyl acetate (3×40 ml). The combined organic layer was washed with saturated aqueous NH4Cl, dried over MgSO4, filtered and concentrated to give a white solid (3.08 g, crude product): $^1$H NMR (400 MHz, CHLOROFORM-d) δ ppm 7.20 (d, J=8.1 Hz, 2H), 6.77 (m, 2H), 5.73 (br. s., 1H), 5.56 (br. s., 1H), 5.25 (d, J=6.6 Hz, 1H), 3.73 (s, 3H), 1.46 (s, 9H) LCMS (ESI) m/e 282.1 [(M+H)+, calcd for C14H20NO5 282.3].

Part B. [(R)-2-Hydroxy-1-(4-hydroxy-phenyl)-ethyl]-carbamic acid t-butyl ester (R)-tert-Butoxycarbonylamino-(4-hydroxy-phenyl)-acetic acid methyl ester (10 mmol), Lithium Boron hydride (1.089 g, 50 mmol) and THF (50 ml) were combined and stirred at room temperature overnight. Ice (20 ml) was added into the reaction mixture with stirring. Saturated citric acid was then added dropwise until no more bubbles were generated. The reaction mixture was transferred to a separatory funnel. The aqueous layer was extracted with ethyl acetate (3×30 ml). The combined organic layers were washed with saturated NH4Cl and water sequentially, then dried over MgSO4, filtered and concentrated to give a white crude solid (2.92 g, crude product) with some impurity: $^1$H NMR (400 MHz, MeOD) δ ppm 7.14 (d, J=8.6 Hz, 2H), 6.76 (d, J=8.6 Hz, 2H), 4.56 (m, 1H), 3.63 (m, 2H), 1.43 (s, 9H); LCMS (ESI) m/e 254.1 [(M+H)+, calcd for C13H20NO4 254.3].

Part C. {(R)-2-Hydroxy-1-[4-((S)-2-methyl-butoxy)-phenyl]-ethyl}-carbamic acid t-butyl ester

[(R)-2-Hydroxy-1-(4-hydroxy-phenyl)-ethyl]-carbamic acid t-butyl ester (10 mmol), (S)-2-methylbutyl bromide (2.60 g, 17 mmol) and Cs2CO3 (7.47 g, 23 mmol) were combined in DMF (50 ml). The reaction mixture was heated at 70° C. overnight. Saturated NH4Cl was added to quench the reaction. The aqueous layer was extracted with ethyl acetate (3×20 ml). The combined organic layers were washed with brine, then dried over MgSO4, filtered and concentrated to give a white crude solid. The crude product was purified via column chromatography on silica gel (0%-50% ethyl acetate in hexanes) to afford the title compound (2.09 g, 65% yield of 3 steps) as a white solid: $^1$H NMR (400 MHz, CHLOROFORM-d) δ ppm 7.22 (d, J=8.6 Hz, 2H), 6.90 (m, 2H), 5.13 (d, J=6.6 Hz, 1H), 4.73 (br. s., 1H), 3.83 (m, 3H), 3.74 (m, 1H), 2.39 (br. s., 1H), 1.87 (m, 1H), 1.58 (m, 1H), 1.42 (m, 9H), 1.29 (m, 1H), 1.01 (m, 3H), 0.96 (m, 3H); LCMS (ESI) m/e 324.2 [(M+H), calcd for C18H30NO4 324.4].

Part D. (1S,2S)-2-Thiophen-2-yl-cyclopropanecarboxylic acid {(R)-2-hydroxy-1-[4-((S)-2-methyl-butoxy)-phenyl]-ethyl}-amide HCl To a solution of {(R)-2-Hydroxy-1-[4-((S)-2-methyl-butoxy)-phenyl]-ethyl}-carbamic acid t-butyl ester (2.09 g 6.47 mmol), in dichloromethane (30 ml) in an ice bath was added 4 M HCl in 1,4-dioxane (10 ml). The final mixture was then stirred at room temperature for 2 hrs. The excessive solvent was removed in vacuum to give a white solid, which was used as it for next step.

Part E. (1S,2S)-2-Thiophen-2-yl-cyclopropanecarboxylic acid {(R)-2-hydroxy-1-[4-((S)-2-methyl-butoxy)-phenyl]-ethyl}-amide To a solution of (1S,2S)-2-Thiophen-2-yl-cyclopropanecarboxylic acid (1.08 g, 6.45 mmol) in dichloromethane (50 ml) in an ice-bath was added oxalyl chloride (6.50 ml, 64.4 mmol), then DMF (0.1 ml) under nitrogen. The reaction mixture was stirred for 30 minutes at 0° C. The excessive solvent was removed on ratovapor and dried under high vacuum for 2 hrs to give (1S,2S)-2-thiophen-2-yl-cyclopropanecarboxylic chloride. In a separated 250 ml round-bottom flask was charged with {(R)-2-hydroxy-1-[4-((S)-2-methyl-butoxy)-phenyl]-ethyl}-amide HCl (6.47 mmol), dichloromethane (60 ml) and triethylamine (4.30 ml, 32.35 mmol) in an ice cold bath under nitrogen. The (1S,2S)-2-Thiophen-2-yl-cyclopropanecarboxylic chloride, made freshly in dichloromethane (10 ml) was added into the reaction mixture dropwise. The final reaction mixture was stirred for 1.5 hrs at room temperature. The finished reaction was quenched with water. The organic phase was washed with brine (3×30 ml), dried over $MgSO_4$, filtrated, concentrated in vacuum and purified via column chromatography on silica gel with a gradient of 0%-100% of ethyl acetate in hexane to give a white solid (1.42 g, 58% yield): $^1$H NMR (400 MHz, CHLOROFORM-d) δ ppm 7.25 (d, J=8.6 Hz, 2H), 7.09 (m, 1H), 6.91 (m, 3H), 6.82 (d, J=3.5 Hz, 1H), 6.23 (d, J=6.1 Hz, 1H), 5.06 (td, J=6.3, 4.3 Hz, 1H), 3.91 (m, 2H), 3.78 (m, 2H), 2.75 (m, 2H), 1.88 (m, 1H), 1.70 (m, 2H), 1.58 (m, 1H), 1.29 (m, 2H), 1.03 (d, J=6.8 Hz, 3H), 0.96 (t, J=7.5 Hz, 3H); LCMS (ESI) m/e 374.2 $[(M+H)^+$, calcd for $C_{21}H_{28}NO_3S$ 374.5].

Example 7

(1S,2S)-2-Thiophen-2-yl-cyclopropanecarboxylic acid {(R)-1-[4-(2-ethyl-butoxy)-phenyl]-2-hydroxy-ethyl}-amide

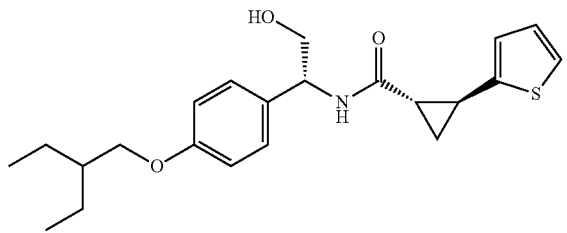 [SMILES: CCC(CC)COc1ccc([C@H](CO)NC(=O)[C@H]2C[C@@H]2c2cccs2)cc1]

Part A. [(R)-2-Hydroxy-1-(4-methoxy-phenyl)-ethyl]-carbamic acid benzyl ester

To 1.88 g (12.4 mmol) of benzylcarbamate suspended in 16 mL n-propanol was added 12.2 mL 1 N NaOH (12.2 mmol), and freshly prepared $^t$BuOCl (1.4 mL, 12.2 mmol) and then stirred for 8 min at rt. It was then cooled to 0° C. followed by the addition of the catalyst (DHQD)$_2$PHAL (156 mg, 0.2 mmol) dissolved in 14 mL n-PrOH. This was followed by the addition of the styrene (538 uL, 4 mmol) also dissolved in 20 mL n-PrOH, and stirred for another 8 min. Then $K_2OsO_4.2H_2O$ (58.8 mg, 0.16 mmol) was added directly, and the resulting mixture stirred for 1.5 hr at 0° C. Several color changes were observed, from brown, to bright red, to orange and then finally light yellow. Dilute with EtOAc, and quench with aq. $Na_2S_2O_3$. The organic layer was separated and the aqueous layer extracted with EtOAc. The combined organic layers were washed with brine, dried over $MgSO_4$, and concentrated. It was purified by flash column 20-40% EtOAc/hexanes to obtain 761 mg (63%) of the product.

Part B. (R)-2-Amino-2-(4-methoxy-phenyl)-ethanol

A mixture of [(R)-2-Hydroxy-1-(4-methoxy-phenyl)-ethyl]-carbamic acid benzyl ester (761 mg, 2.53 mmol) and Pd/C (76 mg) in MeOH (8 mL) was stirred under $H_2$ (1 atm) for 1.5 h. The mixture was filtered and the filtrate was concentrated to give the titled compound (432 mg, 100%).

Part C. (1S,2S)-2-Thiophen-2-yl-cyclopropanecarboxylic acid [(R)-2-hydroxy-1-(4-methoxy-phenyl)-ethyl]-amide A solution of (1S,2S)-2-thiophen-2-yl-cyclopropanecarbonyl chloride (0.78 mmol in 3 ml of DCM, generated as in Example 6) was added to a solution of (R)-2-amino-2-(4-methoxy-phenyl)-ethanol (130.3 mg, 0.78 mmol) in DCM (3 mL), followed by DIEA (277.2 uL, 1.56 mmol). The reaction was quenched with $H_2O$/EtOAc and work up. The organic layer was dried ($MgSO_4$) and the solvent was removed. The residue was subjected to flash column to afford the titled compound (105 mg, 43%).

Part D. (1S,2S)-2-Thiophen-2-yl-cyclopropanecarboxylic acid [(R)-2-hydroxy-1-(4-hydroxy-phenyl)-ethyl]-amide To a suspension of (1S,2S)-2-thiophen-2-yl-cyclopropanecarboxylic acid [(R)-2-hydroxy-1-(4-methoxy-phenyl)-ethyl]-amide (105 mg, 0.331 mmol) in DCM (3 mL) at −10° C. was added $BBr_3$ (1M, 0.994 mL, 0.994 mmol). The mixture was stirred between −10 to −5° C. for 1 h. Work up with $NaHCO_3$/HCl to give the crude product which was further purified by flash column (5% MeOH in DCM) of give the titled product (70 mg, 70%).

Part E. (1S,2S)-2-Thiophen-2-yl-cyclopropanecarboxylic acid {(R)-2-hydroxy-1-[4-(2-ethyl-butoxy)-phenyl]-2-hydroxy-ethyl}-amide To a solution of (1S,2S)-2-thiophen-2-yl-cyclopropanecarboxylic acid [(R)-2-hydroxy-1-(4-hydroxy-phenyl)-ethyl]-amide (35 mg, 0.105 mmol) dissolved in 0.8 mL DMF was added the 2-ethylbutyl bromide (38 mg, 0.231 mmol) followed by $K_2CO_3$ (32 mg, 0.231 mmol). It was heated to 60° C. with stirring overnight. On the next day it was cooled to rt, diluted with ether and quenched with water. The organic layer was washed with water and brine, dried over $MgSO_4$, and concentrated. It was then purified by flash column (20-40% EtOAc in DCM) to afford the titled compound (26 mg, 58%). $^1$H NMR (400 MHz, MeOD) δ ppm 5.8 (d, J=8.6 Hz, 2H), 5.7 (dd, J=5.2, 1.1 Hz, 1H), 5.4 (d, J=8.6 Hz, 3H), 5.3 (d, J=3.5 Hz, 1H), 3.4-3.5 (m, 1H), 2.4 (d, J=5.6 Hz, 2H), 2.2 (dd, J=6.6, 3.0 Hz, 2H), 1.0 (dd, J=6.3, 2.5 Hz, 1H), 0.5 (ddd, J=8.6, 4.7, 4.4 Hz, 1H), 0.1-0.2 (m, 1H), −0.1-0.1 (m, J=15.1, 7.7, 7.6, 7.6 Hz, 5H), −0.2 (ddd, J=8.5, 6.2, 4.3 Hz, 1H), −0.5 (t, J=7.5 Hz, 6H). LRMS (ESI)=388, $[(M+1)^+$ calcd for $C_{22}H_{30}NO_3S$ 387.5].

Example 8

(1S,2S)-2-Thiophen-2-yl-cyclopropanecarboxylic acid {(R)-1-[4-(2-ethyl-butoxy)-2-methyl-phenyl]-2-hydroxy-ethyl}-amide

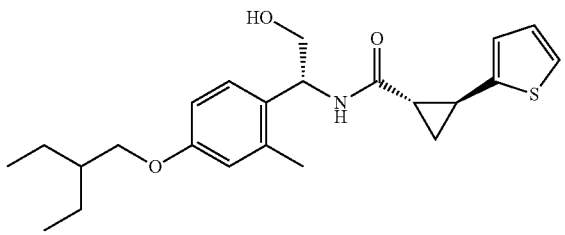 [SMILES: CCC(CC)COc1ccc([C@H](CO)NC(=O)[C@H]2C[C@@H]2c2cccs2)c(C)c1]

This example was prepared as Example 7 starting with 4-methoxy-2-methyl-1-vinyl-benzene. $^1$H NMR (400 MHz, MeOD) δ ppm 7.2 (d, J=8.8 Hz, 1H), 7.1 (dd, J=5.1, 1.3 Hz, 1H), 6.9 (t, J=3.5 Hz, 1H), 6.8 (d, J=2.8 Hz, 1H), 6.7-6.8 (m, 2H), 5.2 (dd, J=7.6, 5.8 Hz, 1H), 3.9 (d, J=5.6 Hz, 2H), 3.6-3.7 (m, 2H), 2.5 (dd, J=5.7, 4.2 Hz, 1H), 2.4 (s, 3H), 2.0 (ddd, J=8.6, 4.7, 4.4 Hz, 1H), 1.6-1.7 (m, 1H), 1.4-1.6 (m, 5H), 1.2 (ddd, J=8.4, 6.1, 4.4 Hz, 1H), 0.9 (t, J=7.5 Hz, 6H). LRMS (ESI)=402, [(M+1)$^+$ calcd for $C_{23}H_{32}NO_3S$ 401.6].

Example 9

(1S,2S)-2-Thiophen-2-yl-cyclopropanecarboxylic acid {(R)-2-hydroxy-1-[2-methyl-4-((S)-2-methyl-butoxy)-phenyl]-ethyl}-amide

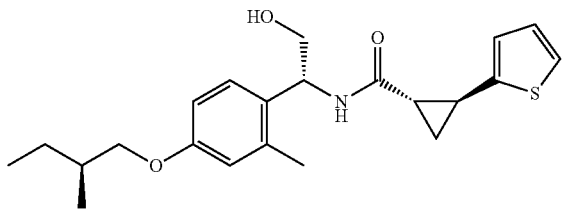 [SMILES: CC[C@H](C)COc1ccc([C@H](CO)NC(=O)[C@H]2C[C@@H]2c2cccs2)c(C)c1]

Part A. 4-Benzyloxy-2-methyl-1-vinyl-benzene

To a suspension methyltriphenyl-phosphonium bromide (18.95 g, 53.05 mmol) in 150 mL THF at 0° C. was added 31.8 mL (50.84 mmol) of 1.6 M nBuLi. The resulting mixture was stirred at 0° C. for 1 hr, followed by a slow addition of the aldehyde (10.0 g, 44.21 mmol) dissolved in 40 mL THF. The ice bath was removed, and stirred for 2 hr at rt. It was then diluted with ether and quench with water. The organic layer was washed with brine and dried over MgSO$_4$. It was purified in the ISCO using 1-5 EtOAc/hex to obtain 9.67 g (97%) of the styrene. $^1$H NMR (400 MHz, CHLOROFORM-d) δ ppm 7.33-7.48 (m, 6H), 6.90 (dd, J=17.4, 10.9 Hz, 1H), 6.80-6.85 (m, 2H), 5.56 (dd, J=17.4, 1.5 Hz, 1H), 5.21 (dd, J=10.9, 1.5 Hz, 1H), 5.09 (s, 2H), 2.36 (s, 3H).

Part B. [(R)-1-(4-Benzyloxy-2-methyl-phenyl)-2-hydroxy-ethyl]-carbamic acid tert-butyl ester To 15.36 g (131.1 mmol) of tert-butoxycarbamate suspended in 100 mL propanol was added 150 mL 0.87 M NaOH (131.1 mmol), and freshly prepared $^t$BuOCl (14.9 g 131.1 mmol) and then stirred for 8 min at rt. It was then cooled to 0° C. followed by the addition of the catalyst (DHQD)$_2$PHAL (2.0 g, 2.59 mmol) dissolved in 30 mL PrOH. This was followed by the addition of the styrene (9.64 g, 42.99 mmol) also dissolved in 20 mL PrOH, and stirred for another 8 min. Then K$_2$OsO$_4$.2H$_2$O was added directly, and the resulting mixture stirred for 1.5 hr at 0° C. Several color changes were observed, from brown, to bright red, to orange and then finally light yellow. Dilute with EtOAc, and quench with aq. Na$_2$S$_2$O$_3$. The organic layer was separated and the aqueous layer extracted with EtOAc. The combined organic layers were washed with brine, dried over MgSO$_4$, and concentrated. It was purified on the ISCO using 5-50% EtOAc/hex to obtain 8.5 g (55%) of the product.

Part C. [(R)-2-Hydroxy-1-(4-hydroxy-2-methyl-phenyl)-ethyl]-carbamic acid tert-butyl ester To a 500 mL flask containing the benzyl protected phenol (1.48 g, 4.15 mmol) dissolved 45 mL MeOH was added Pd—C (0.35 g, 0.33 mmol). The air was removed and the reaction vigorously stirred under a balloon of hydrogen gas. After 2 hr, it was filtered through a pad of diatomaceous earth (Celite®), and concentrated to obtain 984 mg (88%) of the product. $^1$H NMR (400 MHz, CHLOROFORM-d) δ ppm 7.37-7.47 (m, 4H), 7.31-7.37 (m, 1H), 7.25-7.30 (m, 2H), 7.16 (d, J=8.3 Hz, 1H), 6.78-6.87 (m, 2H), 6.71-6.77 (m, 1H), 4.88-5.02 (m, 1H), 3.81 (br. s., 2H), 2.38 (s, 3H), 1.33-1.52 (m, 9H); m/e LCMS calcd 358.2 [(M+1)$^+$, for $C_{21}H_{22}NO_4$ 357.2].

Part D. {(R)-2-Hydroxy-1-[2-methyl-4-((S)-2-methyl-butoxy)-phenyl]-ethyl}-carbamic acid tert-butyl ester To a solution of the phenol compound (969 mg, 3.36 mmol) dissolved in 10 mL DMF was added the alkyl bromide (658 mg, 4.36 mmol) followed by K$_2$CO$_3$ (753 mg, 5.46 mmol). It was heated to 50° C. with stirring overnight. On the next day it was cooled to rt, diluted with ether and quenched with water. The organic layer was washed with water and brine, dried over MgSO$_4$, and concentrated. It was then purified in the ISCO using 5-50 EtOAc/hex to obtain 1.17 g (96%) of the product.

Part E. (R)-2-Amino-2-[2-methyl-4-((S)-2-methyl-butoxy)-phenyl]-ethanol

The Boc-protected aminoalcohol (1.15 g, 3.41 mmol) was dissolved in 25 mL of MeOH and cooled to 0° C. Then acetyl chloride (2.68 g, 34.1 mmol) was slowly added, and the reaction stirred at 0° C. for 4 hr. It was concentrated to obtain HCl salt of the amine (933 mg, 100%). $^1$H NMR (400 MHz, MeOD) δ ppm 7.28-7.36 (m, 1H), 6.83-6.88 (m, 2H), 4.54 (dd, J=8.8, 4.3 Hz, 1H), 3.71-3.88 (m, 4H), 2.40 (s, 3H), 1.79-1.89 (m, 1H), 1.59 (ddd, J=13.4, 7.6, 5.6 Hz, 1H), 1.30 (dt, J=13.6, 7.6 Hz, 1H), 1.03 (d, J=6.6 Hz, 3H), 0.97 (t, J=7.5 Hz, 3H); m/e LCMS calcd 238.1 [(M+1)$^+$, for $C_{14}H_{23}NO_2$ 237.1].

Part F. (1S,2S)-2-Thiophen-2-yl-cyclopropanecarboxylic acid {(R)-2-hydroxy-1-[2-methyl-4-((S)-2-methyl-butoxy)-phenyl]-ethyl}-amide To the (1S,2S)-2-Thiophen-2-yl-cyclopropanecarboxylic acid (300 mg, 1.78 mmol) dissolved in 15 mL THF was added 1,1-carbonyldiimidazole (318 mg, 1.96 mmol) and stirred at rt for 2 hr, followed by the aminoalcohol 16 (488 mg, 1.78 mmol) and TEA (0.273 mL, 1.96 mmol). The resulting mixture was stirred overnight. The reaction mixture was diluted EtOAc and quenched with water. The organic layer was washed with brine, dried over MgSO$_4$ and concentrated. The crude was subjected to ISCO eluting with 10-70% EtOAc in hexane to obtain 521 mg (75%) of the product. $^1$H NMR (400 MHz, CHLOROFORM-d) δ ppm 7.16 (d, J=8.3 Hz, 1H), 7.09 (dd, J=5.1, 1.0 Hz, 1H), 6.88-6.94 (m, 1H), 6.73-6.83 (m, 3H), 6.19 (d, J=6.3 Hz, 1H), 5.27 (td, J=6.6, 4.0 Hz, 1H), 3.78-3.94 (m, 3H), 3.73 (d, J=6.3 Hz, 1H), 3.05 (dd, J=6.8, 5.1 Hz, 1H), 2.67-2.75 (m, 1H), 2.40 (s, 3H), 1.87 (dq, J=13.1, 6.5 Hz, 1H), 1.67-1.74 (m, 2H), 1.52-1.60 (m, 1H), 1.22-1.32 (m, 2 H), 1.02 (d, J=6.8 Hz, 3H), 0.96 (t, J=7.5 Hz, 3H) m/e LCMS calcd 388.3 [(M+1)+, for $C_{22}H_{30}NO_3S$ 388.5].

Example 10

(1S,2S)-2-Thiophen-2-yl-cyclopropanecarboxylic acid {(R)-2-hydroxy-1-[2-methyl-4-(2-methyl-pentyloxy)-phenyl]-ethyl}-amide

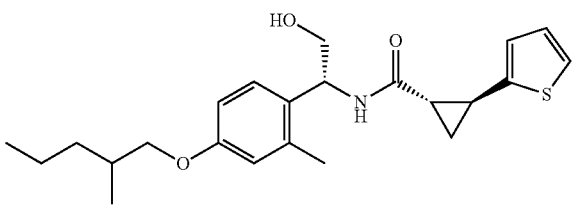 [SMILES: CCCC(C)COc1ccc([C@H](CO)NC(=O)[C@H]2C[C@@H]2c2cccs2)c(C)c1]

This example was prepared as Example 7 starting with 4-methoxy-2-methyl-1-vinyl-benzene and alkylated with 2-methylpentyl bromide. $^1$H NMR (400 MHz, MeOD) δ ppm 7.2-7.3 (m, 1H), 7.1 (dd, J=5.2, 1.1 Hz, 1H), 6.9 (t, J=3.7 Hz, 1H), 6.8 (d, J=3.5 Hz, 1H), 6.7-6.8 (m, 2H), 5.2 (dd, J=7.6, 5.8 Hz, 1H), 3.8-3.8 (m, 1H), 3.7 (dd, J=9.2, 6.4 Hz, 1H), 3.6-3.7 (m, 2H), 2.5 (dd, J=6.3, 2.5 Hz, 1H), 2.4 (s, 3H), 2.0 (ddd, J=8.8, 4.7, 4.5 Hz, 1H), 1.8-2.0 (m, 1H), 1.3-1.6 (m, 4H), 1.2-1.3 (m, 2H), 1.0 (d, J=6.6 Hz, 3H), 0.9 (t, J=7.5 Hz, 3H). LRMS (ESI)=402, [(M+1)+ calcd for $C_{23}H_{32}NO_3S$ 401.6].

Example 11

(1S,2S)-2-Thiophen-2-yl-cyclopropanecarboxylic acid [(R)-1-[4-(2-methyl-pentyloxy)-phenyl]-2-(4-methyl-piperazin-1-yl)-ethyl]-amide

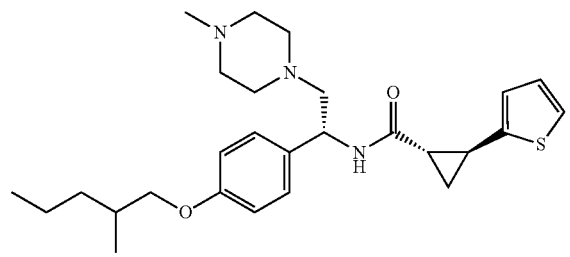 [SMILES: CCCC(C)COc1ccc([C@H](CN2CCN(C)CC2)NC(=O)[C@H]2C[C@@H]2c2cccs2)cc1]

Part A. (R)-tert Butoxycarbonylamino-(4-hydroxy-phenyl)-acetic acid

To a mixture of D-(p-hydroxyphenyl)-glycine (3 g, 18 mmol), NaOH (1 N, 18 mL, 18 mmol) in dioxane (18 mL) was added a solution of (Boc)$_2$O in dioxane (18 mL). The resulting mixture was stirred at rt until the reaction was done (monitored by LC-MS). The product (2.54 g) was crystallized.

Part B. (R)-tert Butoxycarbonylamino-[4-(tert-butyl-dimethyl-silanyloxy)-phenyl]-acetic acid To a solution of (R)-tert Butoxycarbonylamino-(4-hydroxy-phenyl)-acetic acid (2.54 g, 9.55 mmol) in DMF (5 mL) was added imidazole (1.43 g, 21 mmol) followed by t-butyldimethylsilyl chloride (1.58 g, 10.5 mmol). The resulting mixture was stirred at rt for overnight. Additional t-butyldimethylsilyl chloride (1.43 g, 9.55 mmol) was added and let the reaction continue for another hour. The reaction mixture was diluted with EtOAc and washed with H$_2$O three times and concentrated. To the residue was added aqueous 1N NaOH and then acidified with concentrated HCl. The resulting mixture was extracted with EtOAc three times. The combined organic layer was dried (MgSO$_4$) and concentrated to provide the titled compound (4.5 g).

Part C. [(R)-1-[4-(tert-Butyl-dimethyl-silanyloxy)-phenyl]-2-(4-methyl-piperazin-1-yl)-2-oxy-ethyl]-carbamic acid tert-butyl ester To a solution of (R)-tert butoxycarbonylamino-[4-(tert-butyl-dimethyl-silanyloxy)-phenyl]-acetic acid (2.5 g, 6.79 mmol) in DMF (10 ml) at 0° C. was added EDCI (1.56 g, 8.15 mmol) followed by HOAt (1.11 g, 8.15 mmol). After 15 min., N-methyl piperazine (0.9 ml, 8.15 mmol) was added and the resulting mixture was warmed up to rt and stirred for overnight. The mixture was poured into H$_2$O/EtOAc and the layers were separated. The organic layer was washed twice with H$_2$O and then dried (MgSO$_4$). After removal of the solvent, the residue was purified by flash column (2.5-5% MeOH in DCM) to give the titled compound (785 mg, 26%).

Part D. [(R)-1-[4-(tert-Butyl-dimethyl-silanyloxy)-phenyl]-2-(4-methyl-piperazin-1-yl)-ethyl]-carbamic acid tert-butyl ester To a slurry of [(R)-1-[4-(tert-butyl-dimethyl-silanyloxy)-phenyl]-2-(4-methyl-piperazin-1-yl)-2-oxy-ethyl]-carbamic acid tert-butyl ester (785 mg, 1.69 mmol) in THF (5 ml) at 0° C. was added BH$_3$.THF (1 M, 3.4 ml, 3.4 mmol) dropwise. The mixture was warmed up to 40° C. and stirred overnight (the reaction went to dry). Additional THF (5 ml) and BH$_3$.THF (3.4 mL) was added and the resulting mixture was stirred at 50° C. for overnight. The reaction was quenched with H$_2$O and stirred for 10 min. The mixture was then extracted with EtOAc three times. The combined EtOAc layer was dried (MgSO$_4$). After removal of the solvent, the residue was purified by flash column (25% EtOAc in hexane) to give the titled compound as a white solid (370 mg, 48%).

Part E. [(R)-1-(4-Hydroxy-phenyl)-2-(4-methyl-piperazin-1-yl)-ethyl]-carbamic acid tert-butyl ester To a solution of [(R)-1-[4-(tert-butyl-dimethyl-silanyloxy)-phenyl]-2-(4-methyl-piperazin-1-yl)-ethyl]-carbamic acid tert-butyl ester (370 mg, 0.82 mmol) in THF (3 ml) was added TBAF (1M in THF, 1 ml, 1 mmol). The resulting mixture was stirred at rt for 3 h. The reaction mixture was diluted with ether and quenched with aq. NH$_4$Cl. The organic layer was washed with water and brine, and then dried over MgSO$_4$. Removal of the solvent provided the titled compound.

Part F. [(R)-1-[4-(2-Methyl-pentyloxy)-phenyl]-2-(4-methyl-piperazin-1-yl)-ethyl]-carbamic acid tert-butyl ester A mixture of [(R)-1-(4-hydroxy-phenyl)-2-(4-methyl-piperazin-1-yl)-ethyl]-carbamic acid tert-butyl ester (57 mg, 0.17 mmol), K$_2$CO$_3$ (72 mg, 0.52 mmol) and 2-methylpenthyl bromide (60 ul, 0.42 mmol) in DMF (1 ml) was stirred at 55° C. for over night. After cool to rt, the mixture was diluted with EtOAc and washed with H₂O and dried (MgSO₄). Removal of the solvent provided the titled compound. MS (MH⁺).

Part G. (1S,2S)-2-Thiophen-2-yl-cyclopropanecarboxylic acid [(R)-1-[4-(2-methyl-pentyloxy)-phenyl]-2-(4-methyl-piperazin-1-yl)-ethyl]-amide A solution of [(R)-1-[4-(2-methyl-pentyloxy)-phenyl]-2-(4-methyl-piperazin-1-yl)-ethyl]-carbamic acid tert-butyl ester (~0.17 mmol) in MeOH (1 ml) was treated with HCl in dioxane (4 M, 0.85 ml, 3.4 mmol) for 1 h. The mixture was concentrated and dissolved in DCM (1 ml). To this solution was added TEA (50 µl, 0.34 mmol) was added followed by a solution of (1S,2S)-2-phenyl-cyclopropanecarbonyl chloride in DCM (1 M, 0.19 mL, 0.19 mmol, generated as in Example 1). The resulting reaction mixture was stirred at RT for 1.5 h. Water was added and the aqueous layer was extracted by dichloromethane. Organic layer was dried (MgSO₄) and concentrated. The residue was purified by preparative HPLC to afford the titled compound (15.4 mg). ¹H NMR (400 MHz, MeOD) δ ppm 7.2 (d, J=8.6 Hz, 2H), 7.0 (dd, J=5.2, 1.1 Hz, 1H), 6.8-6.9 (m, 3H), 6.7 (d, J=3.3 Hz, 1H), 5.0 (dd, J=9.3, 5.3 Hz, 1H), 3.7-3.8 (m, 1H), 3.6-3.7 (m, 1H), 3.2-3.3 (m, 6H), 2.8-2.9 (m, 2H), 2.8 (s, 3H), 2.6 (dd, J=13.1, 5.6 Hz, 2H), 2.4 (dd, J=6.2, 2.7 Hz, 1H), 1.7-2.0 (m, 2H), 1.2-1.5 (m, 4H), 1.0-1.2 (m, J=10.2, 4.0, 4.0, 3.8 Hz, 2H), 0.9 (d, J=6.8 Hz, 3H), 0.8 (t, 3H). LRMS (ESI)=470, [(M+1)⁺ calcd for C₂₂H₄₀N₃O₂S 469.7].

Example 12

(1S,2S)-2-Thiophen-2-yl-cyclopropanecarboxylic acid [(R)-2-hydroxy-1-(3-methoxy-4'-methyl-biphenyl-4-yl)-ethyl]-amide

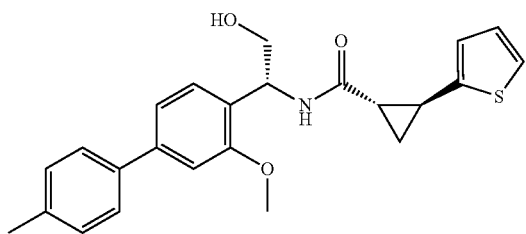 [SMILES: COc1cc(-c2ccc(C)cc2)ccc1[C@H](CO)NC(=O)[C@H]1C[C@@H]1c1cccs1]

Part A. [(R)-1-(4-Benzyloxy-2-methoxy-phenyl)-2-hydroxy-ethyl]-carbamic acid benzyl ester To 2.12 g (13.95 mmol) of benzylcarbamate suspended in 18 mL n-propanol was added 12.73 mL 1 N NaOH (13.73 mmol), and freshly prepared ᵗBuOCl (1.75 mL, 13.73 mmol) and then stirred for 8 min at rt. It was then cooled to 0° C. followed by the addition of the catalyst (DHQD)₂PHAL (175 mg, 0.225 mmol) dissolved in 15.75 mL n-PrOH. This was followed by the addition of the styrene (1.08 g, 4.5 mmol) also dissolved in 22.5 mL n-PrOH, and stirred for another 8 min. Then K₂OsO₄·2H₂O (66.2 mg, 0.18 mmol) was added directly, and the resulting mixture stirred for 1.5 hr at 0° C. Several color changes were observed, from brown, to bright red, to orange and then finally light yellow. Dilute with EtOAc, and quench with aq. Na₂S₂O₃. The organic layer was separated and the aqueous layer extracted with EtOAc. The combined organic layers were washed with brine, dried over MgSO₄, and concentrated. It was purified on the ISCO using 5-50% EtOAc/hex to obtain 1.2 g (66%) of the product.

Part B. 4-((R)-1-Amino-2-hydroxy-ethyl)-3-methoxy-phenol

A mixture of [(R)-1-(4-Benzyloxy-2-methoxy-phenyl)-2-hydroxy-ethyl]-carbamic acid benzyl ester (1.2 g, 2.96 mmol) and Pd/C (120 mg) in MeOH/EtOAc (5:1, 10 mL) was stirred under H₂ (1 atm) for overnight. The mixture was filtered and the filtrate was concentrated to give the titled compound (542 mg, 100%).

Part C. [(R)-2-Hydroxy-1-(4-hydroxy-2-methoxy-phenyl)-ethyl]-carbamic acid benzyl ester A mixture of 4-((R)-1-amino-2-hydroxy-ethyl)-3-methoxy-phenol (542 mg, 2.96 mmol), benzylchloroformate (634 uL, 4.44 mmol) and NaHCO₃ (497 mg, 5.92 mmol) in THF/H₂O (15/10 mL) was stirred at rt for overnight. After aqueous work up, the titled compound (736.3 mg, 79%) was obtained by flash column (5-7% MeOH in DCM).

Part D. {(R)-1-[4-(tert Butyl-dimethyl-silanyloxy)-2-methoxy-phenyl]-2-hydroxy-ethyl}-carbamic acid benzyl ester A mixture of [(R)-2-hydroxy-1-(4-hydroxy-2-methoxy-phenyl)-ethyl]-carbamic acid benzyl ester (736.3 mg, 2.32 mmol), TBSCl (840.2 mg, 5.57 mmol) and imidazole (757.2 mg, 11.1 mmol) in DCM was stirred at rt for 24 h. The reaction was worked up with EtOAc/H₂O. Flash column provided the titled compound (585.7 mg, 59%).

Part E. (1S,2S)-2-Thiophen-2-yl-cyclopropanecarboxylic acid {(R)-1-[4-(tert-butyl-dimethyl-silanyloxy)-2-methoxy-phenyl]-2-hydroxy-ethyl}-amide A mixture of {(R)-1-[4-(tert butyl-dimethyl-silanyloxy)-2-methoxy-phenyl]-2-hydroxy-ethyl}-carbamic acid benzyl ester (585.7 mg, 1.36 mmol) and Pd/C (60 mg) in MeOH (5 mL) was stirred under H₂ (1 atm) for overnight. The mixture was filtered and used directly for next reaction.

To a solution of (1S,2S)-2-thiophen-2-yl-cyclopropanecarboxylic acid (228.2 mg, 1.36 mmol) in dichloromethane (10 ml) in an ice-bath was added oxalyl chloride (0.58 ml, 6.6 mmol), then DMF (0.1 ml) under nitrogen. The reaction mixture was stirred for 30 minutes at 0° C. The excessive solvent was removed on ratovapor and dried under high vacuum for 2 hrs to give (1S,2S)-2-thiophen-2-yl-cyclopropanecarboxylic chloride. In a separated flask was charged with above aminoalcohol (1.36 mmol), dichloromethane (5 ml) and DIEA (448 uL, 2.72 mmol) in an ice cold bath under nitrogen. The (1S,2S)-2-thiophen-2-yl-cyclopropanecarboxylic chloride, made freshly in dichloromethane (10 ml) was added into the reaction mixture dropwise. The final reaction mixture was stirred for 1.5 hrs at room temperature. The finished reaction was quenched with water. The organic phase was washed with brine (3×10 ml), dried over MgSO₄, filtrated, concentrated in vacuum and purified via column chromatography on silica gel with a gradient of 0%-100% of ethyl acetate in hexane to give a white solid (393.4 mg, 59% yield).

Part F. (1S,2S)-2-Thiophen-2-yl-cyclopropanecarboxylic acid [(R)-2-hydroxy-1-(4-hydroxy-2-methoxy-phenyl)-ethyl]-amide To the (1S,2S)-2-Thiophen-2-yl-cyclopropanecarboxylic acid {(R)-1-[4-(tert-butyl-dimethyl-silanyloxy)-2-methoxyphenyl]-2-hydroxy-ethyl}-amide (393.4 mg, 0.88 mmol) dissolved in 20 ml THF at 0° C., was added 1.32 ml TBAF (1.0 M solution, 1.32 mmol). The ice bath was remove and stirred for 2 hr at rt. It was diluted with ether and quenched with aq. NH₄Cl. The organic layer was washed with water and brine, and then dried over MgSO₄. It was concentrated and purified on flash column (6% MeOH in DCM) to obtain the titled compound (used directly for next reaction).

Part G. Trifluoro-methanesulfonic acid 4-{(R)-2-hydroxy-1-[((1S,2S)-2-thiophen-2-yl-cyclopropanecarbonyl)amino]-ethyl}-3-methoxy-phenyl ester A suspension of (1S,2S)-2-thiophen-2-yl-cyclopropanecarboxylic acid [(R)-2-hydroxy-1-[4-hydroxy-2-methoxy-phenyl)-ethyl]-amide (~0.88 mmol), N-phenyl-bis(trifluoromethanesulonimide) (471.6 mg, 1.32 mmol) and TEA (366 ul, 2.64 mmol) in THF (5 ml) was stirred over the weekend. The reaction mixture was diluted with H₂O and extracted with EtOAc. The EtOAc layer was washed with NaHCO₃ and brine, and dried (MgSO₄). After removal of the solvent, the residue was purified by flash column (15-80% EtOAc in hexane) to provided the titled compound as an off white solid (342.4 mg, 84%).

Part H. (1S,2S)-2-Thiophen-2-yl-cyclopropanecarboxylic acid [(R)-2-hydroxy-1-(3-methoxy-4'-methyl-biphenyl-4-yl)-ethyl]-amide A mixture of trifluoro-methanesulfonic acid 4-{(R)-2-hydroxy-1-[((1S,2S)-2-thiophen-2-yl-cyclopropanecarbonyl)amino]-ethyl}-3-methoxy-phenyl ester (66 mg, 0.142 mmol), tolylboronic acid (38.1 mg, 0.284 mmol), Pd(PPh₃)₄ (16.4 mg, 0.014 mmol) and Na₂CO₃ (45.2 mg, 0.426 mmol) in DME/H₂O (1.2/0.4 mL) was heated at 80° C. for 3 h. The reaction mixture was passed through a short silica pad (EtOAc) and concentrated. The residue was subjected to preparative HPLC to give the titled compound (12.3 mg). ¹H NMR (400 MHz, MeOD) δ ppm 7.7 (d, J=8.3 Hz, 2H), 7.6 (d, J=8.3 Hz, 1H), 7.5 (d, J=7.8 Hz, 2H), 7.4 (t, J=5.4 Hz, 2H), 7.1-7.2 (m, 1H), 7.1 (d, J=3.5 Hz, 1H), 5.6 (dd, J=7.8, 4.5 Hz, 1H), 4.8 (s, 1H), 4.2 (s, 3H), 4.0 (dd, J=11.1, 4.5 Hz, 1H), 3.9 (dd, J=11.4, 7.8 Hz, 1H), 2.8 (dd, J=6.3, 2.5 Hz, 1H), 2.6 (s, 3H), 2.3 (dd, J=8.0, 4.7 Hz, 1H), 1.8 (ddd, J=9.2, 4.8, 4.7 Hz, 1H), 1.5 (ddd, 1H). LRMS (ESI)=408, [(M+1)⁺ calcd for C₂₄H₂₆NO₃S 407.5].

Example 13

(1S,2S)-2-Thiophen-2-yl-cyclopropanecarboxylic acid [(R)-1-(4'-ethyl-3-methoxy-biphenyl-4-yl)-2-hydroxy-ethyl]-amide

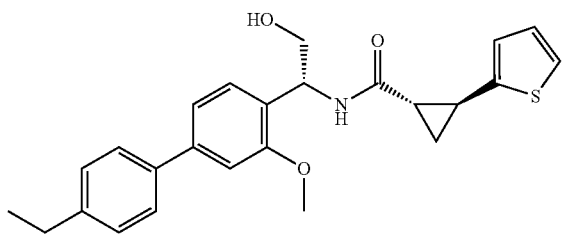 [SMILES: CCc1ccc(-c2ccc([C@H](CO)NC(=O)[C@H]3C[C@@H]3c3cccs3)c(OC)c2)cc1]

This example was prepared same as Example 12. Final coupling was done with 4-ethylphenylbronic acid. ¹H NMR (400 MHz, MeOD) δ ppm 7.5 (d, J=8.1 Hz, 2H), 7.3 (d, J=8.3 Hz, 1H), 7.3 (d, J=8.3 Hz, 2H), 7.1-7.2 (m, 2H), 6.9 (dd, J=5.2, 3.4 Hz, 1H), 6.9 (d, J=3.3 Hz, 1H), 5.4 (dd, J=7.8, 4.5 Hz, 1H), 4.6-4.7 (m, 1H), 4.0 (s, 3H), 3.8 (dd, J=11.2, 4.7 Hz, 1H), 3.7 (dd, J=11.4, 7.8 Hz, 1H), 2.7 (q, J=7.6 Hz, 2H), 2.5 (ddd, J=9.2, 5.6, 4.2 Hz, 1H), 2.1 (ddd, J=8.3, 5.3, 4.0 Hz, 1H), 1.6 (ddd, J=9.5, 4.6, 4.3 Hz, 1H), 1.3 (t, J=7.6 Hz, 4H). LRMS (ESI)=422.2, [(M+1)⁺ calcd for C₂₅H₂₈NO₃S 421.6].

Example 14

(1S,2S)-2-Thiophen-2-yl-cyclopropanecarboxylic acid [(R)-2-hydroxy-1-(2-methoxy-4-pent-1-ynyl-phenyl)-ethyl]-amide

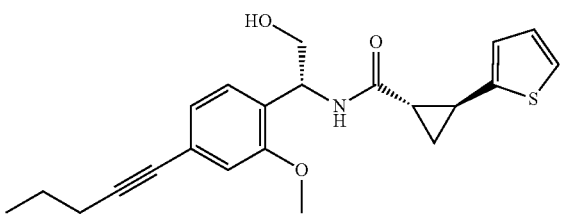 [SMILES: CCCC#Cc1ccc([C@H](CO)NC(=O)[C@H]2C[C@@H]2c2cccs2)c(OC)c1]

This example was prepared same as Example 12. Final coupling was done as follows:

A mixture of trifluoro-methanesulfonic acid 4-{(R)-2-hydroxy-1-[((1S,2S)-2-thiophen-2-yl-cyclopropanecarbonyl)amino]-ethyl}-3-methoxy-phenyl ester (86 mg, 0.185 mmol), 1-pentyne (73 ul, 0.74 mmol), Pd(PPh₃)₄ (21.4 mg, 0.019 mmol), CuI (7 mg, 0.037 mmol) and n-propylamine (46 ul, 0.555 mmol) in toluene (2 mL) was heated at 80° C. for 5 h. Additional 1-pentyne (73 ul) was added and the reaction was continued for 48 h at 80° C. The reaction mixture was diluted with EtOAc and washed with H₂O. The EtOAc layer was dried (MgSO₄) and concentrated. The residue was subjected to flash column (20-30% EtOAc in hexane) then preparative HPLC to give the titled compound (22 mg, 31%). MS (MH⁺). ¹H NMR (400 MHz, CHLOROFORM-d) δ ppm 7.2 (d, J=8.1 Hz, 1H), 7.1 (d, J=5.3 Hz, 1H), 6.9 (t, J=3.3 Hz, 2H), 6.9 (dd, J=5.1, 3.5 Hz, 1H), 6.8 (d, J=3.5 Hz, 1H), 5.3 (dd, J=7.6, 4.5 Hz, 1H), 3.8 (s, 3H), 3.7 (dd, J=11.1, 4.5 Hz, 1H), 3.6 (dd, J=11.2, 7.7 Hz, 1H), 2.5 (dd, J=9.2, 3.9 Hz, 1H), 2.4 (t, J=7.1 Hz, 2H), 2.1 (ddd, J=8.6, 4.7, 4.4 Hz, 1H), 1.6-1.7 (m, 2H), 1.5 (ddd, J=9.2, 4.8, 4.7 Hz, 1H), 1.2 (ddd, J=8.3, 6.1, 4.3 Hz, 1 H), 1.0 (t, J=7.3 Hz, 3H). LRMS (ESI)=384, [(M+1)⁺ calcd for C₂₂H₂₆NO₃S 383.5].

Example 15

(1S,2S)-2-Thiophen-2-yl-cyclopropanecarboxylic acid {(R)-2-hydroxy-1-[4-(2-methyl-pentyloxy)-phenyl]-ethyl}-amide

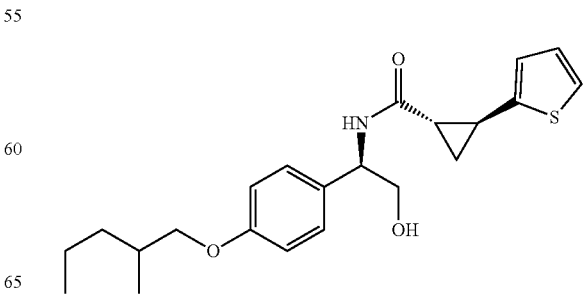

Part A. 1-Benzyloxy-4-vinyl-benzene

To a suspension of methyl triphenylphosphonium bromide in THF (75 ml) at 0° C. was added 1.6M n-butyl lithium in THF (17.69 ml, 28.30 mmol). The mixture was stirred under nitrogen for 1 hr; then a solution of 4-benzyloxy-benzaldye (5.00 g, 23.58 mmol) in THF (40 ml) was added into the mixture. The final reaction mixture was stirred for 1 hr at 0° C. and 2 hrs at room temperature. The reaction was then quenched by adding saturated ammonium chloride (100 ml) and water (20 ml). The aqueous phase was extracted by ethyl acetate (3×30 ml). The combined organic layers were washed with brine, then dried over $MgSO_4$, filtered and concentrated to give a pale yellow crude solid. The crude product was purified via column chromatography on silica gel (0%-5% of ethyl acetate in hexanes) to afford a white solid (3.06 g, 62% yield): $^1$H NMR (400 MHz, CHLOROFORM-d) δ ppm 7.31 (m, 7H), 6.86 (m, 2H), 6.59 (dd, J=17.7, 10.9 Hz, 1H), 5.55 (m, 1H), 5.05 (m, 1H), 5.00 (s, 2H); LCMS (ESI) m/e 211.1 [(M+H), calcd for $C_{15}H_{15}O$ 211.3].

Part B. [(R)-1-(4-Benzyloxy-phenyl)-2-hydroxy-ethyl]-carbamic acid t-butyl ester To a solution of t-butyl carbamate (3.65 g, 30.5 mmol) in n-propanol (40 ml) was added the solution of sodium hydroxide (1.26 g, 30.5 mmol) in water (75 ml), then added t-butyl hypochloride (3.5 ml, 30.5 mmol), made freshly (Org. Syn. 184) in a light-off hood. The mixture was stirred for 5 minutes at room temperature. This reaction mixture was then placed in an ice-bath, (DHQD)$_2$PHAL (0.492 g, 0.6 mmol) in n-propanol (40 ml) and 1-Benzyloxy-4-vinyl-benzene (2.10 g, 10 mmol) in n-propanol (70 ml) were added sequentially, stirred for 6 minutes. $K_2OsO_2$ $2H_2O$ (0.147 g, 0.4 mmol) was added directly at 0° C. The final reaction mixture was stirred for 1.5 hrs to generate a light yellow clear solution. A saturated solution of sodium sulfite (100 ml) was added to quench the reaction at 0° C. Excessive n-propanol was removed in a high vacuum. The aqueous phase was extracted by ethyl acetate (3×30 ml). The combined organic layers were washed with brine (2×30 ml), then dried over $MgSO_4$, filtered and concentrated to give a yellow crude solid. The crude product was purified via column chromatography on silica gel with a gradient of 0%-100% of ethyl acetate in hexanes to afford a white solid (2.01 g, 59% yield, about 13% of regio-isomer): $^1$H NMR (400 MHz, CHLOROFORM-d) δ ppm 7.39 (m, 5H), 7.23 (d, J=8.8 Hz, 2H), 6.98 (d, J=8.6 Hz, 2H), 5.15 (d, J=5.6 Hz, 1H), 5.07 (s, 2H), 4.74 (d, J=1.0 Hz, 1H), 3.84 (t, J=5.3 Hz, 2H), 2.37 (br. s., 1H), 1.42 (m, 9H); LCMS (ESI) m/e 344.2 [(M+H), calcd for $C_{20}H_{26}NO_4$ 344.4].

Part C. [(R)-2-Hydroxy-1-(4-hydroxy-phenyl)-ethyl]-carbamic acid t-butyl ester

[(R)-1-(4-Benzyloxy-phenyl)-2-hydroxy-ethyl]-carbamic acid t-butyl ester (2.013 g, 5.87 mmol) and 10% Palladium on active carbon (0.300 g, 0.294 mmol) were mixed in ethanol (15 ml) and dichloromethane (5 ml). The hydrogenation was carried at 1 atmosphere at room temperature overnight. The catalyst was filtered out. The filtrate was concentrated to a white solid (1.350 g, 91% yield): $^1$H NMR (400 MHz, MeOD) δ ppm 7.36 (d, 2H), 6.97 (m, 2H), 3.83 (m, 1H), 3.54 (dt, J=3.2, 1.5 Hz, 2 H), 1.66 (m, 9H); LCMS (ESI) m/e 254.1 [(M+H), calcd. for $C_{13}H_{20}NO_4$ 254.3].

Part D. {(R)-2-Hydroxy-1-[4-(2-methyl-pentyloxy)-phenyl]-ethyl}-carbamic acid t-butyl ester

[(R)-2-Hydroxy-1-(4-hydroxy-phenyl)-ethyl]-carbamic acid t-butyl ester (0.700 g 2.77 mmol), 2-methylpentyl bromide (0.548 g, 3.32 mmol) and $Cs_2CO_3$ (1.17 g, 3.59 mmol) were combined in DMF (15 ml). The reaction mixture was heated at 70° C. overnight. Saturated $NH_4Cl$ was added to quench the reaction. The aqueous layer was extracted with ethyl acetate (3×10 ml). The combined organic layers were washed with brine, then dried over $MgSO_4$, filtered and concentrated to give a white crude solid. The crude product was purified via column chromatography on silica gel (0%-50% ethyl acetate in hexanes) to afford the title compound (0.705 g, 76% yield of 2 steps) as a white solid: $^1$H NMR (400 MHz, CHLOROFORM-d) δ ppm 7.21 (d, 2H), 6.89 (d, J=8.6 Hz, 2H), 5.18 (d, J=7.1 Hz, 1H), 4.72 (br. s., 1 H), 3.81 (dd, J=9.0, 5.7 Hz, 3H), 3.72 (m, 1H), 3.49 (s, 2H), 2.54 (br. s., 1H), 1.95 (m, 1H), 1.35 (m, 11H), 1.02 (d, J=6.8 Hz, 3H), 0.93 (m, 3H); LCMS (ESI) m/e 338.2 [(M+H), calcd for $C_{19}H_{32}NO_4$ 338.5].

Part E. (R)-2-Amino-2-[4-(2-methyl-pentyloxy)-phenyl]-ethanol HCl

To a solution of {(R)-2-Hydroxy-1-[4-(2-methyl-pentyloxy)-phenyl]-ethyl}-carbamic acid t-butyl ester (0.70 g 2.08 mmol), in dichloromethane (10 ml) in an ice bath was added 4 M HCl in 1,4-dioxane (10 ml). The final mixture was then stirred at room temperature for 1.5 hrs. The excessive solvent was removed in vacuum to give a white solid, which was used directly for next step.

Part F. (1S,2S)-2-Thiophen-2-yl-cyclopropanecarboxylic acid {(R)-2-hydroxy-1-[4-(2-methyl-pentyloxy)-phenyl]-ethyl}-amide To a solution of (1S,2S)-2-Thiophen-2-yl-cyclopropanecarboxylic acid (0.110 g, 0.66 mmol) in dichloromethane (10 ml) in an ice-bath was added oxalyl chloride (0.58 ml, 6.60 mmol), then DMF (0.1 ml) under nitrogen. The reaction mixture was stirred for 30 minutes at 0° C. The excessive solvent was removed on ratovapor and dried under high vacuum for 2 hrs to give (1S,2S)-2-thiophen-2-yl-cyclopropanecarboxylic chloride. In a separated 50 ml round-bottom flask was charged with (R)-2-Amino-2-[4-(2-methyl-pentyloxy)-phenyl]-ethanol HCl (0.47 mmol), dichloromethane (6 ml) and triethylamine (0.31 ml, 2.35 mmol) in an ice cold bath under nitrogen. The (1S,2S)-2-Thiophen-2-yl-cyclopropanecarboxylic chloride, made freshly in dichloromethane (10 ml) was added into the reaction mixture dropwise. The final reaction mixture was stirred for 1.5 hrs at room temperature. The finished reaction was quenched with water. The organic phase was washed with brine (3×10 ml), dried over $MgSO_4$, filtrated, concentrated in vacuum and purified via column chromatography on silica gel with a gradient of 0%-100% of ethyl acetate in hexane to give a white solid (0.088 g, 48% yield): $^1$H NMR (400 MHz, CHLOROFORM-d) δ ppm 7.14 (m, 2H), 6.99 (dd, J=5.2, 1.1 Hz, 1H), 6.81 (m, 3 H), 6.72 (d, J=3.3 Hz, 1H), 6.14 (d, J=6.3 Hz, 1H), 4.95 (m, 1H), 3.80 (m, 2H), 3.67 (m, 2H), 2.72 (dd, J=7.1, 4.8 Hz, 1H), 2.62 (m, 1H), 1.85 (m, 1H), 1.60 (m, 2H), 1.27 (m, 5H), 0.92 (d, J=6.8 Hz, 3H), 0.83 (m, 3H); LCMS (ESI) m/e 374.2 [(M+H)$^+$, calcd for $C_{22}H_{30}NO_3S$ 374.5].

Example 16

(1S,2S)-2-Thiophen-2-yl-cyclopropanecarboxylic acid [(R)-1-[4-((S)-2-methyl-butoxy)-phenyl]-2-(4-methyl-piperazin-1-yl)-ethyl]-amide

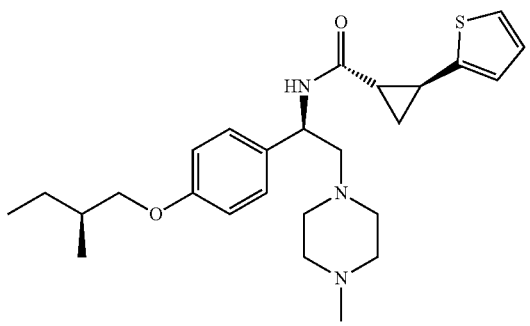

Part A. [(R)-1-[4-((S)-2-Methyl-butoxy)-phenyl]-2-(4-methyl-piperazin-1-yl)-2-oxo-ethyl]-carbamic acid tert-butyl ester To 220 mg (0.627 mmol) of (R)-tert-Butoxycarbonylamino-[4-((S)-2-methyl-butoxy)-phenyl]-acetic acid dissolved in 10 mL DCM was added the amine (125 mg, 1.25 mmol) and DCC (258 mg, 1.25 mmol). It resulting mixture was stirred overnight at rt. It was diluted with DCM and filtered through thin pad of silica gel. It was then concentrated and purified on the ISCO eluting with 0-12% MeOH/DCM to obtain 243 mg (89%) of the product.

Part B. (R)-2-Amino-2-[4-((S)-2-methyl-butoxy)-phenyl]-1-(4-methyl-piperazin-1-yl)-ethanone To 220 mg (0.508 mmol) of [(R)-1-[4-((S)-2-Methyl-butoxy)-phenyl]-2-(4-methyl-piperazin-1-yl)-2-oxo-ethyl]-carbamic acid tert-butyl ester dissolved in 12 mL of MeOH at 0° C., was added AcCl (0.36 mL, 5.081 mmol) and the resulting mixture maintained at 0° C. with stirring for 4 hr. It was then concentrated to obtain the 206 mg (100%) of di-HCl salt.

Part C. (R)-1-[4-((S)-2-Methyl-butoxy)-phenyl]-2-(4-methyl-piperazin-1-yl)-ethylamine To 200 mg (0.49 mmol) of (R)-2-Amino-2-[4-((S)-2-methyl-butoxy)-phenyl]-1-(4-methyl-piperazin-1-yl)-ethanone di-HCl salt in 10 mL of THF was added 5.9 mL LAH (1.0 M solution, 4.9 mmol). The resulting mixture was refluxed overnight. On the next day it was cooled to 0° C. and 0.5 mL of concentrated aq. KOH was slowly added. The ice bath was removed, and allowed it to stir for 1 hr, and then diluted with EtOAc, dried over MgSO$_4$, filter and concentrated to obtain 68 mg (44%) of the product. The product obtained was pure enough to be used for the next step without further purification.

Part D. (1S,2S)-2-Thiophen-2-yl-cyclopropanecarboxylic acid [(R)-1-[4-((S)-2-methyl-butoxy)-phenyl]-2-(4-methyl-piperazin-1-yl)-ethyl]-amide To the (1S,2S)-2-Thiophen-2-yl-cyclopropanecarboxylic acid (21.5 mg, 0.128 mmol) in 10 mL DCM at 0° C. was added oxalyl chloride (41 mg, 0.32 mmol) and 0.1 mL of DMF. The resulting mixture was stirred at 0° C. for 2 hr. It was concentrated to obtain the acid chloride. This was dissolved in 15 mL of DCM and then the amine (39 mg, 0.128 mmol) and TEA (25.9 mg, 0.256 mmol) were added and allowed to stir at rt for 2 hr. It was diluted with DCM and quenched with water. The organic layer was washed with brine, and dried over MgSO$_4$. It was concentrated and purified on the neutral PREP HPLC to obtain 38 mg (65%) of the desired product. $^1$H NMR (400 MHz, CHLOROFORM-d) δ ppm 7.20 (m, J=8.5 Hz, 2H), 7.07-7.10 (m, 1H), 6.91 (dd, J=5.0, 3.5 Hz, 1H), 6.86 (m, J=8.5 Hz, 2H), 6.82 (d, J=3.3 Hz, 1H), 6.66 (d, J=4.8 Hz, 1H), 4.90 (dt, J=10.1, 5.1 Hz, 1H), 3.77-3.83 (m, 1H), 3.68-3.74 (m, 1H), 3.35-3.50 (m, 1H), 2.62-2.67 (m, 3H), 2.51 (br. s., 2H), 2.46 (br. s., 4H), 2.31 (s, 3H), 1.85 (dq, J=13.1, 6.5 Hz, 1H), 1.72-1.78 (m, 1H), 1.48-1.70 (m, 3H), 1.19-1.31 (m, 4H), 1.10-1.18 (m, 1H), 1.01 (d, J=6.8 Hz, 3H), 0.95 (t, J=7.4 Hz, 3H); m/e LCMS calcd 456.2 [(M+1)$^+$, for C$_{26}$H$_{38}$N$_3$O$_2$S 456.2].

Example 17

(1S,2S)-2-Thiophen-2-yl-cyclopropanecarboxylic acid {(R)-2-amino-1-[4-((S)-2-methyl-butoxy)-phenyl]-ethyl}-amide

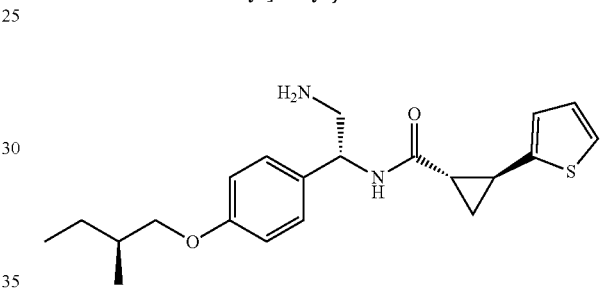

Part A. (R)-Methyl 2-(tert-butoxycarbonylamino)-2-(4-hydroxyphenyl)acetate

A room temperature mixture of (R)-methyl 2-amino-2-(4-hydroxyphenyl)acetate HCl (32 g, 180 mmol), dioxane (360 mL) and water (360 mL) was treated sequentially with triethylamine (100 mL, 720 mmol) and di-tert-butyldicarbonate (47 g, 220 mmol). The reaction was maintained at room temperature for 3 h, then quenched with the addition of an aqueous solution of sodium hydroxide (1 N, 40 mL). The resulting mixture was concentrated to remove dioxane, and the aqueous layer was extracted with Et$_2$O (3×200 mL). The combined organic layers were washed with water (1×200 mL) and brine (1×200 mL), then dried over Na$_2$SO$_4$, filtered and concentrated to afford a semi-solid that was recrystallized from a minimum amount of hot ethyl acetate to afford (R)-Methyl 2-(tert-butoxycarbonylamino)-2-(4-hydroxyphenyl) acetate (40 g, 78% yield) as a white solid: $^1$H NMR (400 MHz, CDCl$_3$) δ 7.23 (d, J=8.0 Hz, 2H), 6.80 (d, J=8.0 Hz, 2H), 5.52 (br s, 1H), 5.26 (br d, 1H), 5.05 (s, 1H), 3.73 (s, 3H), 1.45 (s, 9H); LRMS (ESI) m/e 280.0 [(M−H)$^−$, calcd for C$_{14}$H$_{18}$NO$_5$ 280.3].

Part B. (2R)-Methyl 2-(tert-butoxycarbonylamino)-(4-((S)-2-methyl-butoxy)-phenyl)acetate A 0° C. solution of (R)-Methyl 2-(tert-butoxycarbonylamino)-2-(4-hydroxyphenyl)acetate (2.8 g, 10 mmol), (S)-2-methyl-1-butanol (1.1 mL, 10 mmol), triphenylphosphine (2.6 g, 10 mmol), and tetrahydrofuran (100 mL) was treated dropwise with diisopropylazodicarboxylate (1.9 mL, 10 mmol) via syringe. The resulting reaction mixture was allowed to warm to room temperature and maintained overnight. The reaction was concentrated and the residue was purified by column chromatography on silica gel (5%-10% ethyl acetate in hexanes) to afford (2R)-Methyl 2-(tert-butoxycarbonylamino)-(4-((S)-2-methyl-butoxy)-phenyl)acetate (2.8 g, 80% yield) as a clear, colorless oil: $^1$H NMR (400 MHz, CDCl$_3$) δ 7.27 (d, J=7.3 Hz, 2H), 6.88 (d, J=8.6 Hz, 2H), 5.49 (d, J=6.6 Hz, 1H), 5.26 (d, J=7.3 Hz, 1H), 3.81 (dd, J=9.1, 6.1 Hz, 1H), 3.73 (s, 3H), 3.69-3.76 (m, 1H), 1.86 (dq, J=13.1, 6.5 Hz, 1H), 1.52-1.61 (m, 1H), 1.45 (s, 9H), 1.22-1.33 (m, 2H), 1.02 (d, J=6.8 Hz, 3H), 0.95 (t, J=7.5 Hz, 3H); LRMS (ESI) m/e 352.2 [(M+H)$^+$, calcd for C$_{19}$H$_{30}$NO$_5$ 352.5].

Part C. t-Butyl (R)-2-hydroxy-1-(4-((S)-2-methylbutoxy)phenyl)ethylcarbamate

A room temperature suspension of lithium aluminum hydride (320 mg, 8.5 mmol) and tetrahydrofuran (50 mL) was treated slowly with a solution of (2R)-Methyl 2-(tert-butoxycarbonylamino)-(4-((S)-2-methyl-butoxy)-phenyl)acetate and tetrahydrofuran (40 mL). The resulting reaction mixture was maintained 30 min, and then treated with ethyl acetate (12 mL) and an aqueous solution of potassium hydroxide (10% wt/wt, 24 mL). The mixture was allowed to stir for 1 h, then dried with MgSO$_4$, filtered and concentrated to afford tert-butyl (R)-2-hydroxy-1-(4-((S)-2-methylbutoxy)phenyl) ethylcarbamate (2.2 g, 88% yield) as a yellow solid: $^1$H NMR (400 MHz, CDCl$_3$) δ 7.22 (d, J=8.6 Hz, 2H), 6.90 (d, J=8.8 Hz, 2H), 5.12 (d, J=6.3 Hz, 1H), 4.74 (br. s., 1H), 3.80-3.87 (m, 3H), 3.74 (dd, J=9.1, 6.6 Hz, 1H), 1.87 (dq, J=13.0, 6.5 Hz, 1H), 1.53-1.64 (m, 2H), 1.45 (s, 9H), 1.22-1.34 (m, 1H), 1.03 (d, J=6.6 Hz, 3H), 0.97 (t, J=7.5 Hz, 3H); LRMS (ESI) m/e 324.1 [(M+H)$^+$, calcd for C$_{18}$H$_{30}$NO$_4$ 324.4].

Part D. tert-Butyl (R)-2-(1,3-dioxo-1,3-dihydroisoindol-2-yl)-1-(4-((S)-2-methylbutoxy)phenyl)ethylcarbamate A precooled (0° C.) solution of tert-butyl (R)-2-hydroxy-1-(4-((S)-2-methylbutoxy)phenyl)ethyl carbamate (1.3 g, 4.0 mmol), phthalimide (600 mg, 4.1 mmol), triphenylphosphine (1.1 g, 4.1 mmol) and tetrahydrofuran (40 mL) was treated dropwise via syringe with diisopropylazodicarboxylate (0.80 mL, 4.1 mmol). The resulting reaction mixture was maintained at room temperature overnight, then concentrated and the resulting oil was purified by column chromatography on silica gel (5%-20% ethyl acetate in hexanes) to afford tert-butyl (R)-2-(1,3-dioxo-1,3-dihydroisoindol-2-yl)-1-(4-((S)-2-methylbutoxy)phenyl)ethylcarbamate (800 mg, 45% yield) as a white solid: $^1$H NMR (400 MHz, CDCl$_3$) δ 7.86-7.89 (m, 2H), 7.70-7.75 (m, 2H), 7.26-7.31 (m, 2H), 6.90 (d, J=8.6 Hz, 2H), 5.16-5.24 (m, 1H), 5.04-5.08 (m, 1H), 3.90-3.95 (m, 1H), 3.83 (dd, J=8.6, 5.8 Hz, 1H), 3.74 (dd, J=8.8, 6.6 Hz, 1H), 1.83-1.89 (m, 1H), 1.51-1.61 (m, 2H), 1.26 (s, 9H), 1.25-1.30 (m, 1H), 1.03 (d, J=6.8 Hz, 3H), 0.97 (t, J=7.5 Hz, 3H); LRMS (ESI) m/e 453.2 [(M+H)$^+$, calcd for C$_{26}$H$_{33}$N$_2$O$_5$ 453.6].

Part E. (1S,2S)-2-Thiophen-2-yl-cyclopropanecarboxylic acid {(R)-2-(1,3-dioxo-1,3-dihydro-isoindol-2-yl)-1-[4-((S)-2-methyl-butoxy)-phenyl]-ethyl}-amide A precooled (0° C.) solution of tert-butyl (R)-2-(1,3-dioxo-1,3-dihydroisoindol-2-yl)-1-(4-((S)-2-methylbutoxy)phenyl)ethylcarbamate (250 mg, 0.55 mmol) and dichloromethane (10 mL) was treated dropwise with trifluoroacetic acid (2 mL). The resulting solution was maintained at room temperature for 16 h, then concentrated to afford a yellow oil that was dissolved in dichloromethane (5 mL) and added to a room temperature solution of 2-thiophen-2-yl-cyclopropane carbonylchloride (100 mg, 0.60 mmol), triethylamine (0.20 mL, 1.4 mmol) and dichloromethane (4 mL). The resulting reaction was maintained overnight, then transferred to a separatory funnel and partitioned between ethyl acetate (15 mL) and saturated aqueous sodium bicarbonate (15 mL). The layers were separated, and the aqueous layer was extracted with ethyl acetate (15 mL). The combined organic layers were washed with water (15 mL) and brine (15 mL), then dried (MgSO$_4$), filtered and concentrated to afford a residue that was purified by column chromatography on silica gel (10%-50% ethyl acetate in hexanes) to afford (1S,2S)-2-thiophen-2-yl-cyclopropanecarboxylic acid {(R)-2-(1,3-dioxo-1,3-dihydro-isoindol-2-yl)-1-[4-((S)-2-methyl-butoxy)-phenyl]-ethyl}-amide as a white solid: $^1$H NMR (400 MHz, CDCl$_3$) δ 7.88 (dd, J=5.6, 3.0 Hz, 2H), 7.76 (dd, J=5.6, 3.0 Hz, 2 H), 7.29-7.34 (m, 2H), 7.07 (dd, J=5.2, 1.1 Hz, 1H), 6.87-6.92 (m, 3H), 6.77 (d, J=3.0 Hz, 1H), 6.59 (d, J=7.8 Hz, 1H), 5.29-5.37 (m, 1H), 4.03 (dd, J=14.1, 10.1 Hz, 1H), 3.97 (dd, J=14.1, 4.0 Hz, 1H), 3.81 (dd, J=8.8, 5.8 Hz, 1H), 3.73 (dd, J=9.1, 6.8 Hz, 1H), 2.57 (ddd, J=9.5, 5.9, 4.0 Hz, 1H), 1.86 (dq, J=13.1, 6.5 Hz, 1H), 1.66 (ddd, J=8.4, 5.1, 4.2 Hz, 1H), 1.52-1.63 (m, 2H), 1.23-1.36 (m, 2H), 1.14 (ddd, J=8.3, 6.3, 4.3 Hz, 1H), 1.02 (d, J=6.6 Hz, 3H), 0.96 (t, J=7.5 Hz, 3H).

Part F. (1S,2S)-2-Thiophen-2-yl-cyclopropanecarboxylic acid {(R)-2-amino-1-[4-((S)-2-methyl-butoxy)-phenyl]-ethyl}-amide A mixture of (1S,2S)-2-thiophen-2-yl-cyclopropanecarboxylic acid {(R)-2-(1,3-dioxo-1,3-dihydro-isoindol-2-yl)-1-[4-((S)-2-methyl-butoxy)-phenyl]-ethyl}-amide (330 mg, 0.66 mmol) and ethanol (20 mL) was treated dropwise with hydrazine monohydrate (0.32 mL, 6.6 mmol), and the resulting reaction was maintained at 60° C. overnight. The mixture was allowed to cool to room temperature and the solids were removed by filtration. The filtrate was concentrated to dryness, and triturated with ethyl acetate (15 mL), and the mixture was filtered. The collected solids were air dried, then dissolved in diethyl ether (5 mL). The resulting solution was treated with concentrated HCl (0.1 mL), and the precipitate was collected by filtration to afford (2S)-N-((1R)-2-amino-1-[4-((S)-2-methylbutoxy)phenyl]-ethyl)-2-phenylpropionamide (120 mg, 52% yield) as a white solid: $^1$H NMR (400 MHz, MeOD) δ 7.33 (d, J=8.6 Hz, 2H), 7.16 (dd, J=5.1, 1.3 Hz, 1H), 6.98 (d, J=8.6 Hz, 2 H), 6.89 (dd, J=5.1, 3.5 Hz, 1H), 6.85 (d, J=3.3 Hz, 1H), 5.17 (dd, J=8.7, 5.9 Hz, 1H), 3.86 (dd, J=9.1, 5.8 Hz, 1H), 3.79 (dd, J=9.1, 6.3 Hz, 1H), 3.27-3.31 (m, 2H), 2.57 (ddd, J=9.3, 5.7, 4.2 Hz, 1H), 2.00 (ddd, J=8.3, 5.2, 4.2 Hz, 1H), 1.85 (dq, J=13.1, 6.6 Hz, 1H), 1.55-1.64 (m, 2H), 1.25-1.34 (m, 2H), 1.03 (d, J=6.8 Hz, 3 H), 0.97 (t, J=7.5 Hz, 3H); LRMS (ESI) m/e 373.1 [(M+H)$^+$, calcd for C$_{21}$H$_{29}$N$_2$O$_2$S 373.2].

Example 18

(1S,2S)-2-Thiophen-2-yl-cyclopropanecarboxylic acid {(R)-2-amino-1-[2-methyl-4-((S)-2-methyl-butoxy)-phenyl]-ethyl}-amide

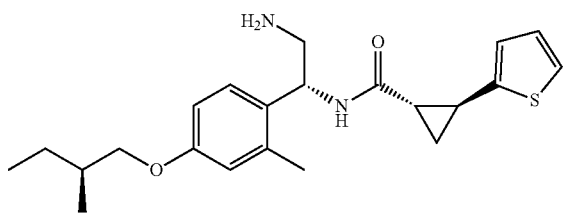 [SMILES: CC[C@H](C)COc1ccc([C@H](CN)NC(=O)[C@H]2C[C@@H]2c2cccs2)c(C)c1]

Example 18 was prepared starting with Example 9.

Part A. (1S,2S)-2-Thiophen-2-yl-cyclopropanecarboxylic acid {(R)-2-(1,3-dioxo-1,3-dihydro-isoindol-2-yl)-1-[2-methyl-4-((S)-2-methyl-butoxy)-phenyl]-ethyl}-amide To a solution of the alcohol (433 mg, 1.12 mmol) and phthalimide (181 mg, 1.23 mmol) in 20 mL of THF was added triphenylphosphine (322 mg, 1.23 mmol). This was cooled to 0° C. and then the DIAD (0.238 mL, 1.23 mmol) was added. The ice bath was removed and stirred at rt for 4 hr. The reaction mixture was concentrated and the crude mixture was purified on the ISCO eluting with 2-40% EtOAc/hex to obtain 393 mg (68%) of the desired product.

Part B. (1S,2S)-2-Thiophen-2-yl-cyclopropanecarboxylic acid {(R)-2-amino-1-[2-methyl-4-((S)-2-methyl-butoxy)-phenyl]-ethyl}-amide To a solution of (1S,2S)-2-Thiophen-2-yl-cyclopropanecarboxylic acid {(R)-2-(1,3-dioxo-1,3-dihydro-isoindol-2-yl)-1-[2-methyl-4-((S)-2-methyl-butoxy)-phenyl]-ethyl}-amide (50 mg, 0.097 mmol) dissolved in 5 mL EtOH was added anhydrous hydrazine (31 mg, 0.97 mmol), and heated to 55° C. for 1 hr with stirring. The reaction mixture was concentrated on the rotavap, and the residue redissolved in EtOAc, and washed with aq. NaHCO$_3$, brine and dried over MgSO$_4$. It was concentrated and purified on the neutral PREP HPLC to obtain 19 mg (51%) of the product. $^1$H NMR (400 MHz, MeOD) δ ppm 8.73-8.68 (d, J=5.2 Hz, 1H), 7.23-7.31 (m, 1H), 7.16 (dd, J=5.1, 1.3 Hz, 1H), 6.89 (dd, J=5.2, 3.4 Hz, 1H), 6.82 (dd, J=4.7, 2.1 Hz, 3H), 5.36-5.48 (m, 1H), 3.68-3.89 (m, 2H), 3.33-3.29 (m, 2H), 2.51-2.60 (m, 1H), 2.40 (s, 3H), 1.98 (d, J=3.7 Hz, 1H), 1.77-1.87 (m, 1H), 1.54-1.66 (m, 2H), 1.23-1.33 (m, 2H), 1.02 (d, 3H), 0.97 (d, J=6.8 Hz, 3H); m/e LCMS calcd 387.3 [(M+1)$^+$, for C$_{22}$H$_{31}$N$_2$O$_2$S 387.3].

BIOLOGICAL ACTIVITY

Materials:

96 well GTPγS assay plates were purchased from Perkin Elmer. Wheat Germ Agglutinin PVT SPA beads and $^{35}$S-GTPγS were purchased from Amersham GDP, GTPγS and all buffer reagents were from Sigma. 384 well white NBS plates were purchased from corning. Pertussis toxin was purchased from Calbiochem. All cell culture reagents were purchased from Invitrogen. Forskolin was purchased from Sigma. The cAMP HTRF kit was purchased fron Cisbio International.

Methods:

GTPγS Assay

The GTPγS assay buffer consisted of 10 mM MgCl$_2$, 180 mM NaCl, 200 uM GDP, 0.167 mg/ml DTT, 1 mM EGTA and 20 mM HEPES pH7.4. This buffer was used for dilution of membranes, beads, and $^{35}$S GTPγS components. To each well of the 96 well assay plate 48 ul assay buffer, 2 ul of 100× compound, 50 ul membrane solution (0.2 ug/ul), 50 ul $^{35}$S GTPγS solution (0.8 nM) and 50 ul of SPA beads (10 mg/ml). Non-specific binding was determined by the addition of cold GTPγS to control wells. The plates were sealed with clear sealing tape and incubated at room temperature for 1 hour. GTPγS activity was detected using a Wallac Micro-Beta Trilux liquid scintillation counter. Non-specific binding was determined using 10 uM cold GTPγS.

cAmp HTRF Assay

The cAMP HTRF assay is modified from the Cisbio International kit procedure 62AM4PEJ. Assay plates were prepared by stamping 0.1 ul of 100× compound stock solutions diluted in DMSO or DMSO alone into 384 well NBS plates. The cAMP HTRF assay was performed using cells in suspension. The cAMP HTRF assay buffer consisted of Hank's Balanced Salt Solution (HBSS), 2 mM CaCl2, 5 mM MgCl2, 20 mM HEPES and 1 mM 3-isobutyl-1-methylxanthine (IBMX) (added fresh at the time of assay). For pertussis toxin treatment pertussis toxin (100 ng/ml) was added to culture medium for 16 hours prior to assay. Confluent cells were disrupted with cell dissociation buffer count cells then centrifuged at 1000×g for minutes. The cell pellet was resuspended in assay buffer alone for basal cAMP measurements or with 0.75 uM forskolin (added immediately prior to addition to wells) for addition to all other wells. Using a Multidrop 384 (Lab systems) 10 ul of cell suspension was added to each well containing compound or DMSO. The plates were incubated at room temperature for 30 minutes covered. During this time the cAMP standard curve was prepared as per manufacturer's instruction. At the end of the incubation 10 ul of anti-cAMP cryptate and 10 ul cAMP-XL, diluted in manufacturer's lysis buffer, were added to each well. The plated were incubated at room temperature for 60 minutes covered then read on an Envision plate reader (Perkin Elmer) and the 665 nm/620 nm fluorescence ratio determined Fluorescence ratio values were converted to molar cAMP concentrations from the standard curve using the GraphPad Prism program.

Table 2 shows EC50 values for select compounds of the present disclosure: All compounds marked "X" had an EC50 of between 62 nM and 130 nM.

| Example Number | Range (EC50) |
|---|---|
| 1 | X |
| 2 | X |
| 3 | X |
| 4 | X |
| 5 | 81 nM |
| 6 | 124 nM |
| 7 | X |
| 8 | X |
| 9 | X |
| 10 | X |
| 11 | X |
| 12 | X |
| 13 | X |
| 14 | X |
| 15 | 74 nM |
| 16 | X |
| 17 | X |
| 18 | X |

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

What is claimed is:

1. A compound of Formula (I)

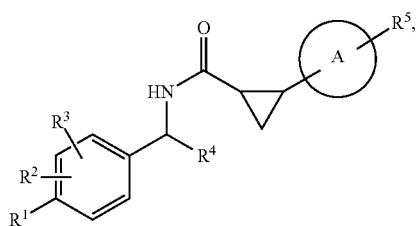

or a pharmaceutically acceptable salt thereof, wherein
A is selected from phenyl and thienyl;
$R^1$ is selected from $C_2$-$C_6$ alkenyl; $C_3$-$C_6$ alkoxy; $C_3$-$C_6$ alkylsulfanyl; $C_2$-$C_6$ alkynyl; $C_3$-$C_6$ cycloalkyl-$C_2$-$C_4$ alkenyl; $C_3$-$C_6$ cycloalkyl-$C_1$-$C_3$ alkoxy; $C_3$-$C_6$ cycloalkyloxy; phenoxy optionally substituted with one $C_1$-$C_3$ alkyl group; phenyl optionally substituted with one, two, or three groups independently selected from $C_1$-$C_3$ alkoxy, $C_1$-$C_3$ alkoxy-$C_1$-$C_3$ alkyl, $C_1$-$C_3$ alkyl, $C_1$-$C_3$ alkylsulfonyl, cyano, halo, and halo-$C_1$-$C_3$ alkyl; phenyl-$C_1$-$C_3$ alkoxy wherein the phenyl part is optionally substituted with one or two groups independently selected from $C_1$-$C_3$ alkyl and halo; and thienyl;
$R^2$ is selected from hydrogen; $C_1$-$C_3$ alkoxy; $C_1$-$C_3$ alkyl; and halo;
$R^3$ is selected from hydrogen and $C_1$-$C_3$ alkoxy;
$R^4$ is selected from $C_1$-$C_3$ alkoxy-$C_1$-$C_3$ alkyl; $C_1$-$C_6$ alkyl; heterocyclyl; hydroxy-$C_1$-$C_3$ alkyl; $(R^aR^bN)$—$C_1$-$C_3$ alkyl;

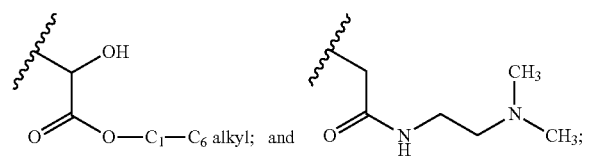

wherein ⌇ denotes the point of attachment to the parent molecular moiety;
$R^5$ is hydrogen; and
$R^a$ and $R^b$ are independently selected from hydrogen and $C_1$-$C_3$ alkyl; or
$R^a$ and $R^b$, together with the nitrogen atom to which they are attached, form a piperidinyl or piperazinyl ring wherein each ring is optionally substituted with one group selected from $C_1$-$C_3$ alkyl and hydroxy-$C_1$-$C_3$ alkyl.

2. The compound of claim 1, or a pharmaceutically acceptable salt thereof, wherein $R^3$ is hydrogen.

3. The compound of claim 2, or a pharmaceutically acceptable salt thereof, wherein A is phenyl.

4. The compound of claim 3, or a pharmaceutically acceptable salt thereof, wherein $R^4$ is selected from $C_1$-$C_3$ alkoxy-$C_1$-$C_3$ alkyl; hydroxy-$C_1$-$C_3$ alkyl; and

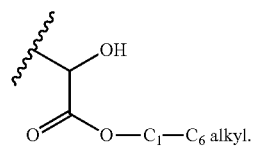

5. The compound of claim 3, or a pharmaceutically acceptable salt thereof, wherein $R^4$ is selected from $C_1$-$C_6$ alkyl and

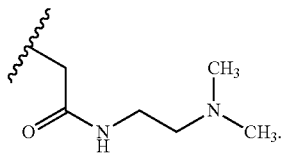

6. The compound of claim 3, or a pharmaceutically acceptable salt thereof, wherein $R^4$ is heterocyclyl.

7. The compound of claim 3, or a pharmaceutically acceptable salt thereof, wherein $R^4$ is $(R^aR^bN)$—$C_1$-$C_3$ alkyl.

8. The compound of claim 2, or a pharmaceutically acceptable salt thereof, wherein A is thienyl.

9. The compound of claim 8, or a pharmaceutically acceptable salt thereof, wherein $R^4$ is selected from $C_1$-$C_3$ alkoxy-$C_1$-$C_3$ alkyl; hydroxy-$C_1$-$C_3$ alkyl; and

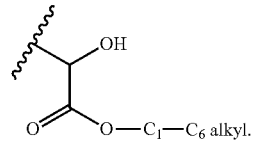

10. The compound of claim 8, or a pharmaceutically acceptable salt thereof, wherein $R^4$ is selected from $C_1$-$C_6$ alkyl and

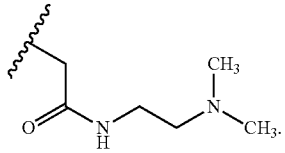 [SMILES: *CC(=O)NCCN(C)C]

11. The compound of claim 8, or a pharmaceutically acceptable salt thereof, wherein $R^4$ is heterocyclyl.

12. The compound of claim 8, or a pharmaceutically acceptable salt thereof, wherein $R^4$ is $(R^aR^bN)$—$C_1$-$C_3$ alkyl.

13. A compound of Formula (II)

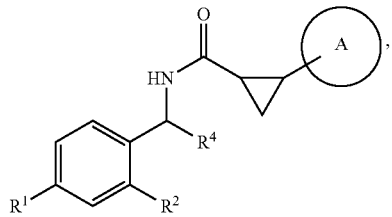

or a pharmaceutically acceptable salt thereof, wherein

A is selected from phenyl and thienyl;

$R^1$ is selected from $C_5$-$C_6$ alkoxy; $C_5$ alkynyl; phenyl optionally substituted with one group selected from $C_1$ alkoxy and $C_1$-$C_2$ alkyl;

$R^2$ is selected from hydrogen; $C_1$ alkoxy and $C_1$ alkyl;

$R^4$ is selected from hydroxy-$C_1$ alkyl and $(R^aR^bN)$—$C_1$ alkyl; and $R^a$ and $R^b$ are each hydrogen; or $R^a$ and $R^b$, together with the nitrogen atom to which they are attached, form a piperazinyl ring substituted with one $C_1$ alkyl group.

14. A compound selected from

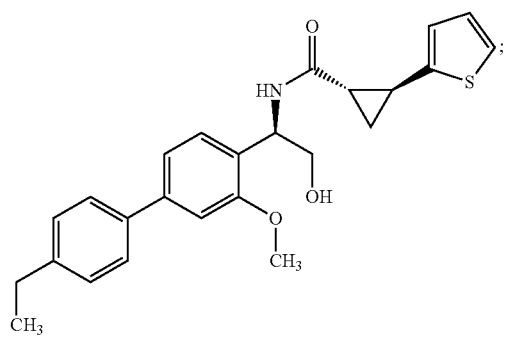

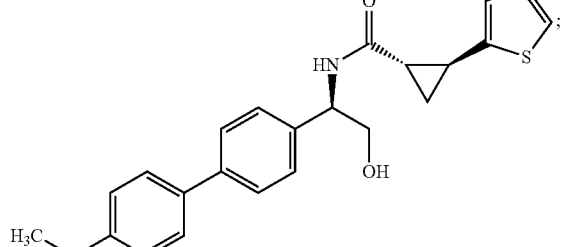

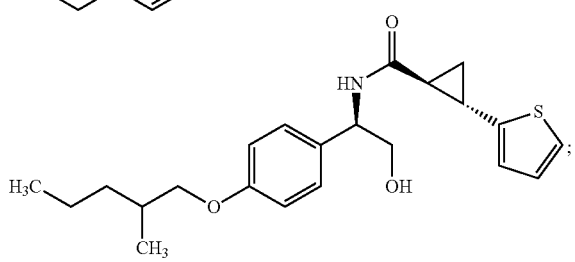

-continued

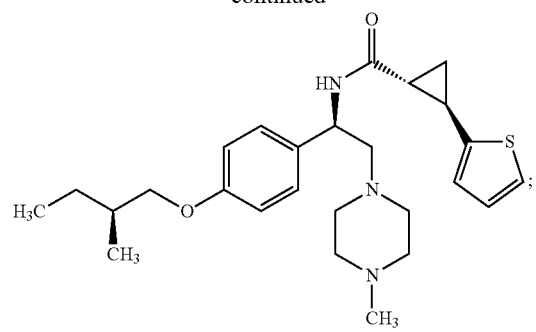

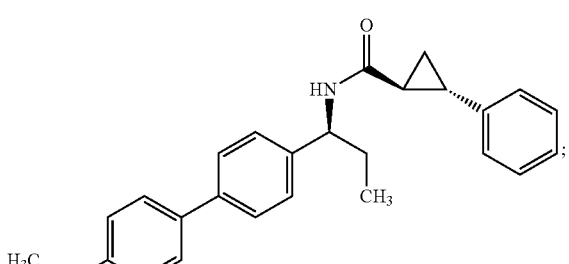

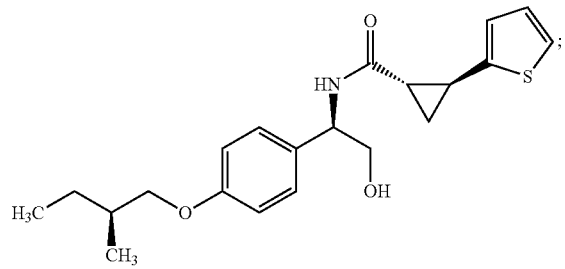

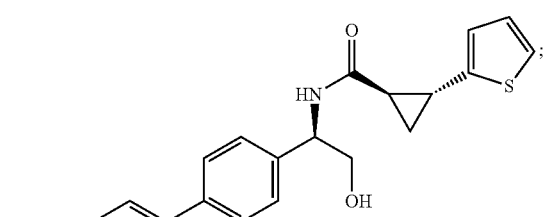

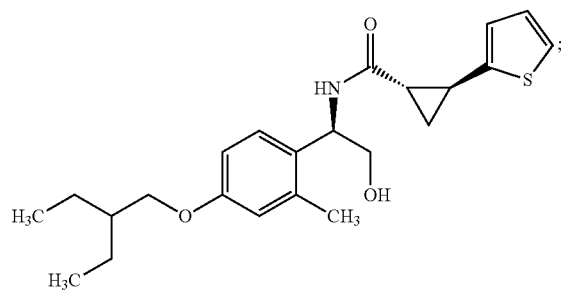

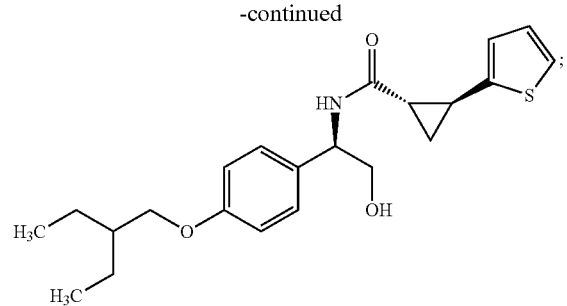
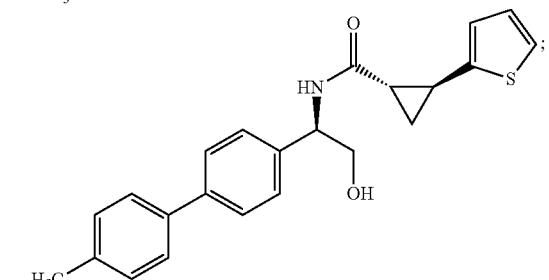
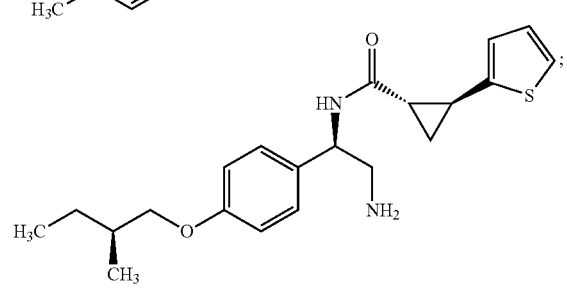
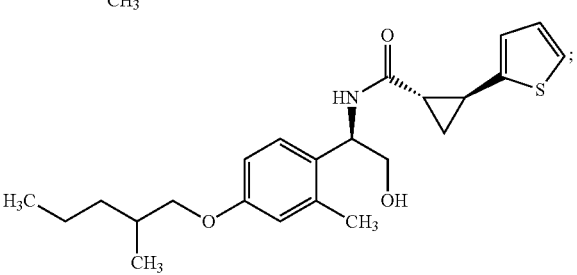
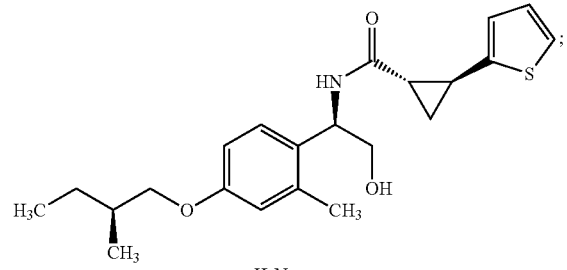
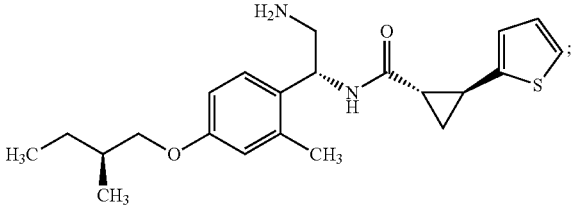
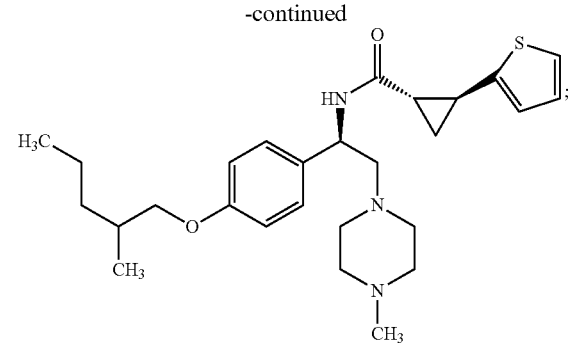
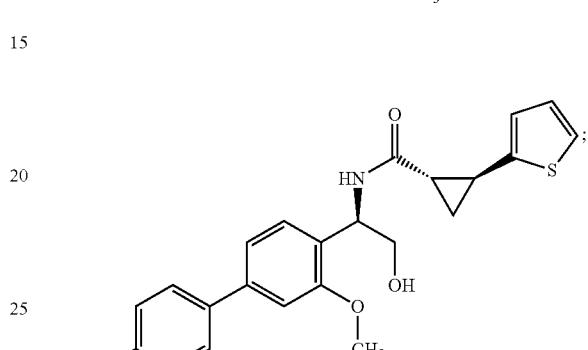
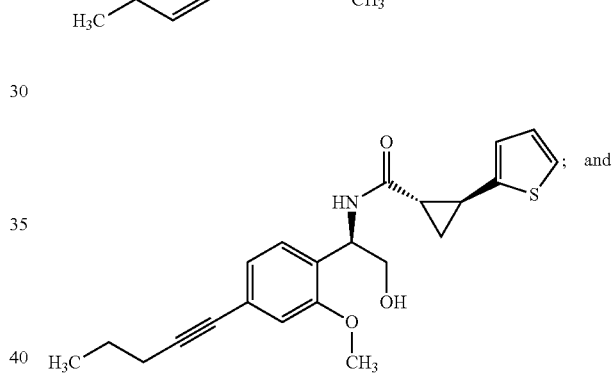
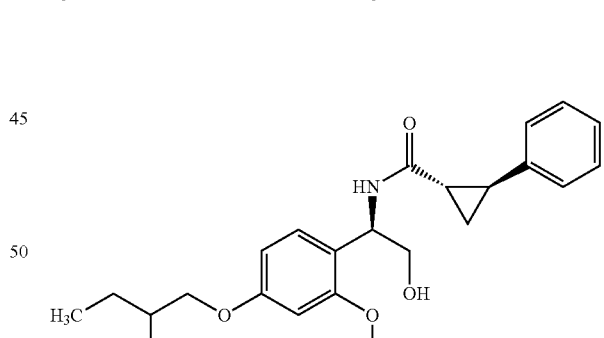
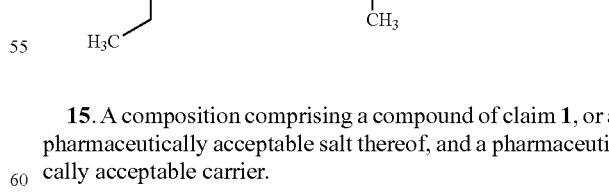
15. A composition comprising a compound of claim 1, or a pharmaceutically acceptable salt thereof, and a pharmaceutically acceptable carrier.
* * * * *